(12) United States Patent
Chung et al.

(10) Patent No.: US 10,631,987 B2
(45) Date of Patent: Apr. 28, 2020

(54) 3D PRINTED TRANS-MODULAR SCAFFOLDS FOR GRAFTING APPLICATIONS IN SEGMENTAL BONE DEFECTS

(71) Applicant: THE TRUSTEES OF THE STEVENS INSTITUTE OF TECHNOLOGY, Hoboken, NJ (US)

(72) Inventors: Rebecca Chung, Hoboken, NJ (US); Antonio Valdevit, Effort, PA (US); Dilhan Kalyon, Teaneck, NJ (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 0 days.

(21) Appl. No.: 15/658,992

(22) Filed: Jul. 25, 2017

(65) Prior Publication Data

US 2018/0177597 A1   Jun. 28, 2018

Related U.S. Application Data

(60) Provisional application No. 62/336,378, filed on Jul. 25, 2016.

(51) Int. Cl.
*A61F 2/28*     (2006.01)
*A61L 27/56*   (2006.01)
(Continued)

(52) U.S. Cl.
CPC ............ *A61F 2/2846* (2013.01); *A61L 27/18* (2013.01); *A61L 27/3608* (2013.01); *A61L 27/3821* (2013.01); *A61L 27/3834* (2013.01); *A61L 27/3847* (2013.01); *A61L 27/3895* (2013.01); *A61L 27/54* (2013.01); *A61L 27/56* (2013.01); *A61L 27/58* (2013.01); *B33Y 10/00* (2014.12); *B33Y 80/00* (2014.12); *C12N 5/0062* (2013.01); *C12N 5/0654* (2013.01); *A61L 2300/412* (2013.01); *A61L 2300/64* (2013.01); *A61L 2300/802* (2013.01); *A61L 2400/18* (2013.01); *A61L 2430/02* (2013.01);
(Continued)

(58) Field of Classification Search
CPC .................................. C12N 5/00; B33Y 80/00
See application file for complete search history.

(56) References Cited

U.S. PATENT DOCUMENTS

| | | | | |
|---|---|---|---|---|
| 2002/0173850 | A1* | 11/2002 | Brodke | A61F 2/30767 623/17.11 |
| 2005/0049706 | A1* | 3/2005 | Brodke | A61F 2/30767 623/17.11 |
| 2011/0307073 | A1* | 12/2011 | Teoh | A61F 2/28 623/23.61 |

* cited by examiner

*Primary Examiner* — Yashita Sharma
(74) *Attorney, Agent, or Firm* — Greenberg Traurig, LLP

(57) ABSTRACT

A bone repair scaffold having two moduli that match those of the cancellous and cortical bone in a patient receiving a bone graft/implant. The bone repair scaffold possesses increased mechanical properties to sustain physiological loading and biologically active capability to facilitate bone fusion. The bone repair scaffold may be 3D-printed, which allows for a variety of scaffold designs and configurations. Pore size, interconnected porosity, shape, and modulus of the bone repair scaffold may be modified for different bone graft applications, whether it is used as filler for bone cancer resections or trauma, or as a fusion device in cases of surgery. Depending on the defect location of the bone shaft, the relative porosity of the scaffold may be modified to account for changes in cortical bone thickness. A method for treating a bone defect using the bone repair scaffold is also disclosed.

20 Claims, 32 Drawing Sheets

(51) Int. Cl.
  *A61L 27/18*   (2006.01)
  *A61L 27/58*   (2006.01)
  *A61L 27/38*   (2006.01)
  *A61L 27/54*   (2006.01)
  *C12N 5/00*    (2006.01)
  *C12N 5/077*   (2010.01)
  *B33Y 80/00*   (2015.01)
  *B33Y 10/00*   (2015.01)
  *A61L 27/36*   (2006.01)

(52) U.S. Cl.
  CPC ...... *C12N 2513/00* (2013.01); *C12N 2527/00* (2013.01); *C12N 2533/40* (2013.01)

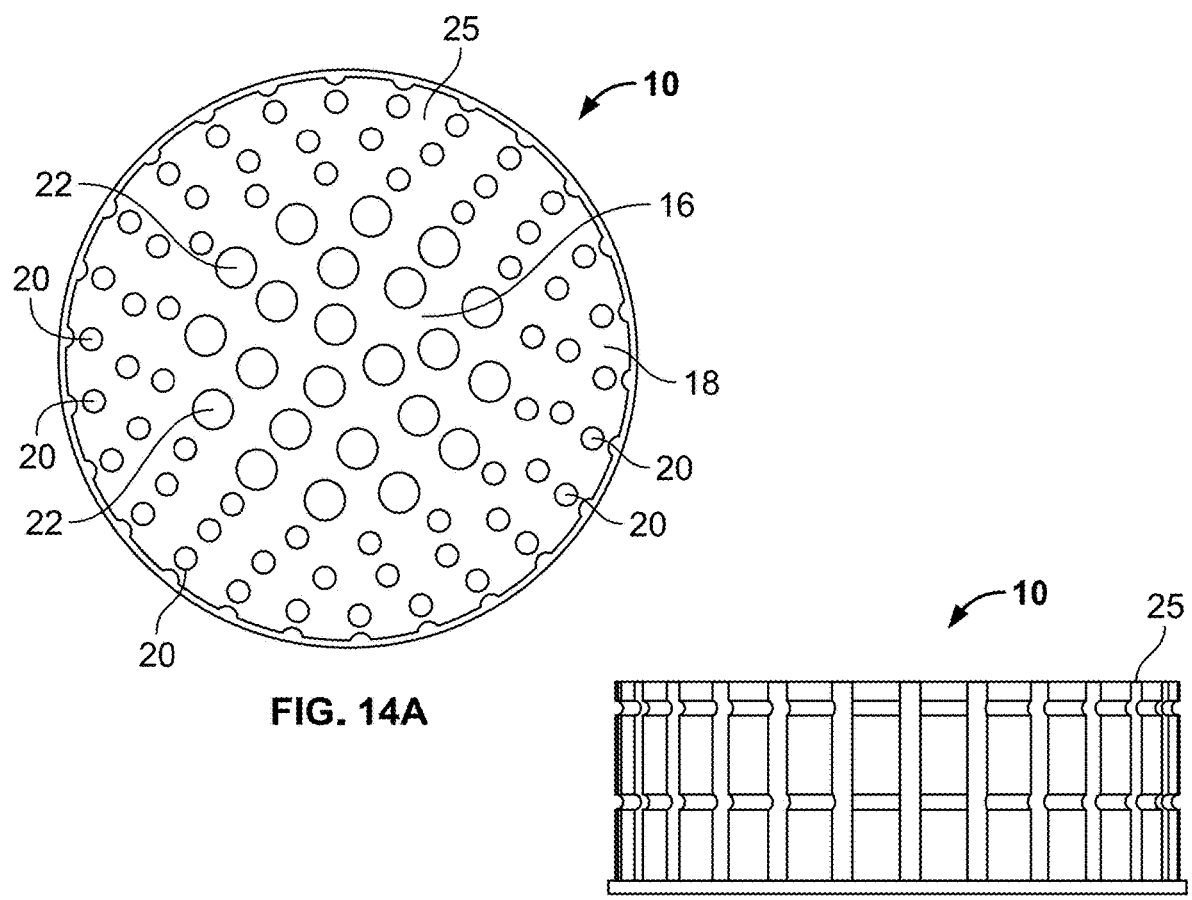
FIG. 14A
FIG. 14B
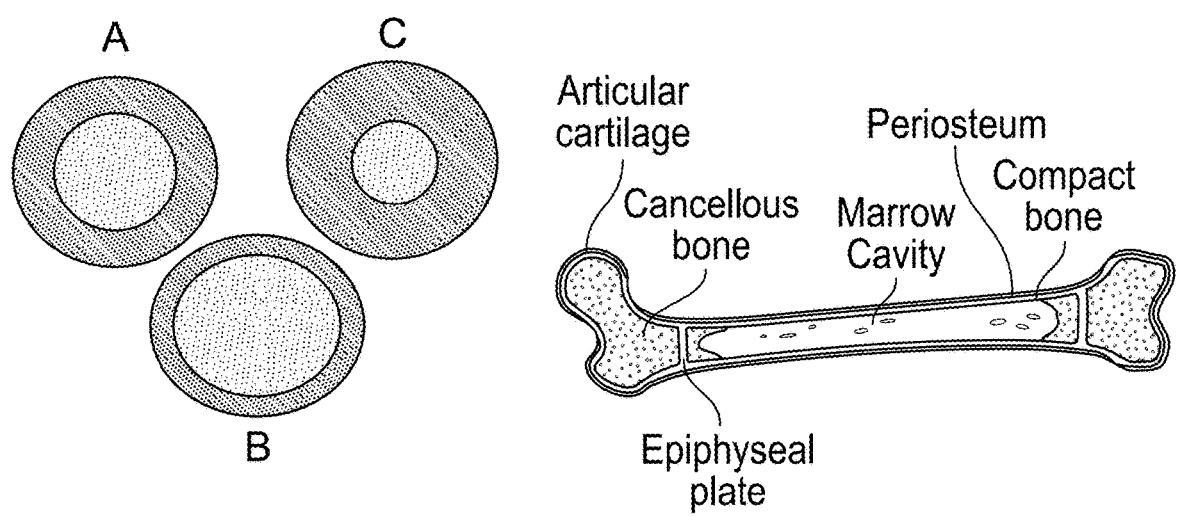
FIG. 15

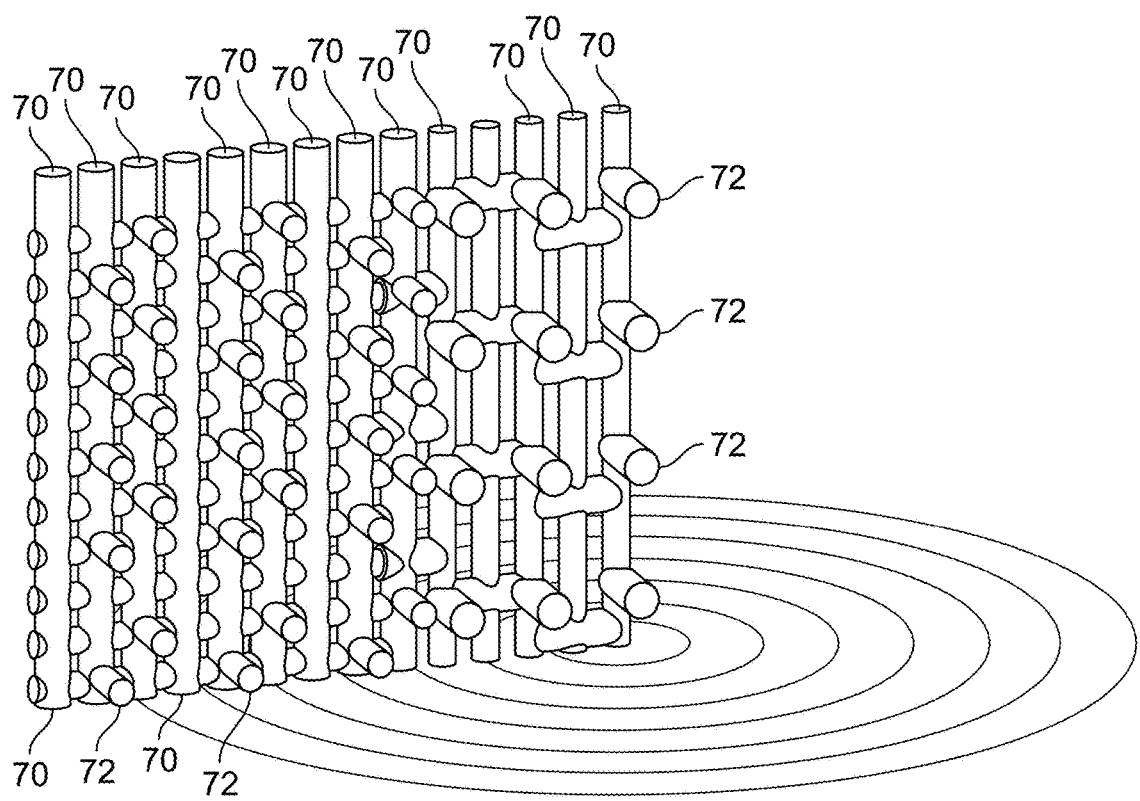
FIG. 17
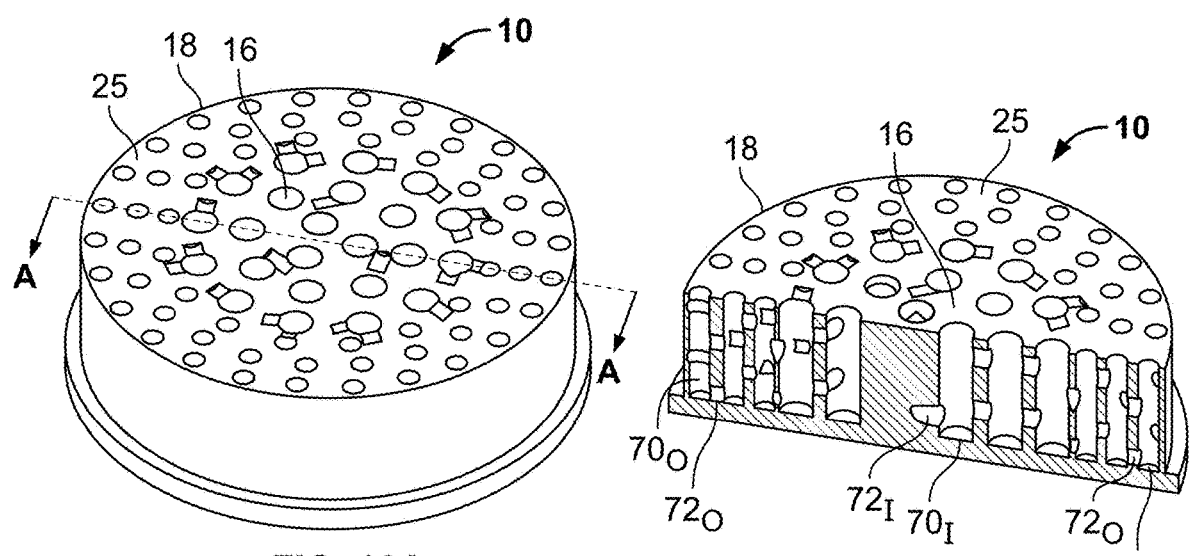
FIG. 18A
FIG. 18B

1. Expand Cells and Grow to Confluency

2. Seed onto Scaffold and Maintain Culture for 1 Week

3. Day 7, Fixate Cells in Scaffold and Stain Methylene Blue

Tilt angle: 0
Lens: 220X100    0.10mm

Tilt angle: 15
Lens: 220X100    0.10mm

3D PRINTED TRANS-MODULAR SCAFFOLDS FOR GRAFTING APPLICATIONS IN SEGMENTAL BONE DEFECTS

RELATED APPLICATION

This is a Section 111(a) application relating to and claiming the benefit of U.S. Provisional Patent Application No. 62/366,378, filed Jul. 25, 2016, the disclosure of which is incorporated by reference in its entirety herein.

FIELD OF INVENTION

The present invention relates to biomedical engineering, and more particularly, to bone repair scaffolds and implants.

BACKGROUND

Bone has remarkable healing properties, but in more complicated conditions where the bone deficiency is greater than 2-3 times its diameter, the process of healing delays or fails. Trauma, bone tumor resections, and congenital deformities are the primary causes of long bone deficiency. As a result, grafting procedures are warranted to facilitate repair and regeneration to restore tissue function.

Bone grafting has become the second most common transplantation procedure, with approximately 2.2 million surgeries performed annually worldwide. Treatment traditionally employs transplanting tissue from one site to another, either in the same patient (autograft) or from a donor (allograft). While these opportunities can be life-saving for patients, the processes to obtain cadaveric graft material pose major risk and difficulties. Harvesting allografts introduce immunological concerns and pose risk of infection and rejection by patients' immune systems. Additionally, harvesting autografts is often costly, painful, and limited by donor site anatomical constraints.

There is a growing need for scaffolds as alternatives for bone graft material to address current shortages in musculoskeletal donor tissue, especially if there is massive segmental bone loss. Tissue-engineered scaffolds have been utilized to enhance the healing response of critically sized bone defects while addressing the drawbacks regarding "gold standard" autograft and allograft use, but overall provide insufficient mechanical support and do not mimic native bone tissue behavior. Improvement to bone grafting procedures with respect to biologically active scaffolds still remains a challenge and there are still no well-approved treatment modalities that satisfy all the requirements to achieve successful and secured healing.

Studies have reported post-operative infection rates as high as 26.3% for allografts and 12.4% for autografts, resulting in surgical revision rates of 47% for allografts and 17% for autografts. Deep infections in bone grafting procedures, such as in limb reconstructions, are a devastating complication and economic burden to both patients and the healthcare system. In tibial fractures alone, the annual incremental medical cost associated with fracture nonunion was $20,364 compared to patients who healed normally.

Alternatively, tissue-engineered biological scaffolds have been utilized as bone graft substitutes to facilitate bridging bone defects to restore tissue function while addressing the disadvantages of traditional grafting methods. However, improving bone grafting procedures with respect to biologically active scaffolds still remains a challenge as traditional fabrication methods are highly complex, involving several steps, and inhibit the ability to control the internal architecture, thereby producing isotropic material with pore sizes that are not always interconnected and do not allow for ample nutrient flow to sustain long term tissue vascularization. Interconnected networks with a porosity of at least 300 µm for bone are required for nutrient exchange and cell mitigation to promote bone regeneration and new tissue growth.

Immunological issues from allografts and local trauma from autograft bone harvesting may be reduced if biologically active, mechanically stable scaffolds are employed. The use of the scaffold of the present invention as alternative bone graft material will provide a better environment for graft incorporation as compared to current traditional methods, as supported by experimental validation, thereby leading to reduced procedure duration, improved bone fusion rates and improved clinical outcomes with respect to patients' return to activity scores.

SUMMARY

In view of the foregoing background, disclosed herein is a bone repair scaffold having an inner core (i.e., inner region) and an outer core (i.e., outer region) surrounding the inner core, wherein the inner core has a first porosity and a first modulus, and the outer core has a second porosity and a second modulus. The second porosity is lower than the first porosity, whereby the second modulus is greater than the first modulus. The first modulus is preferably similar to that of cancellous bone, and the second modulus is preferably similar to that of cortical bone. The first porosity, second porosity and a transition between the first and second porosities constitute a pattern that emulates the porosity pattern of bone. The bone repair scaffold further includes a plurality of horizontal conduits and a plurality of vertical conduits, so as to emulate the internal architecture of bone. The plurality of horizontal conduits includes a first set of horizontal conduits within the inner core, and a second set of horizontal conduits within the outer core, wherein the horizontal conduits of the second set are smaller than the horizontal conduits of the first set. Likewise, the plurality of vertical conduits includes a first set of vertical conduits within the inner core, and a second set of vertical conduits within the outer core, wherein the vertical conduits of the second set are smaller than the vertical conduits of the first set.

The bone repair scaffold is fabricated using biocompatible and biodegradable material, such as polylactic acid (PLA), via 3D-printing, which facilitates a variety of scaffold designs and configurations. Variables such as pore size, interconnected porosity, shape, and modulus may be modified for different bone graft applications, including a filler for bone cancer resections or trauma, or a fusion device in cases of surgery.

A method for repairing a bone defect is also disclosed herein. The method including the steps of (a) fabricating a bone repair scaffold sized and shaped so as to fit in the bone defect, the bone repair scaffold having an inner core and an outer core circumferentially engaging the inner core, the inner core having a first porosity and a first modulus, and the outer core having a second porosity and a second modulus, wherein the second porosity is lower than the first porosity, whereby the second modulus is greater than the first modulus; and (b) implanting the bone repair scaffold in the bone defect.

BRIEF DESCRIPTION OF THE DRAWINGS

For a more complete understanding of the present invention, reference is made to the following detailed description of an embodiment considered in conjunction with the accompanying drawings, in which:

FIG. 14A is a top plan view of a scaffold according to an embodiment of the present invention, as discussed in Example 1A herein;

FIG. 14B is a side elevational view of the scaffold shown in FIG. 14A;

FIG. 15 is a schematic view of the anatomy of a long bone and sectional views of three scaffolds according to the present invention A, B and C, having different relative porosities, as discussed in Example 1A herein;

FIG. 17 is a cutaway view of the scaffold according to an embodiment of present invention, showing the arrangement of vertical and horizontal conduits throughout, as discussed in Example 1B herein;

FIG. 18A is a top perspective view of a scaffold constructed according to an embodiment of the present invention, as discussed in Example 1B herein;

FIG. 18B is a sectional view, taken through line A-A in FIG. 18A, of the scaffold shown in FIG. 18A to reveal the horizontal and vertical conduits thereof, as discussed in Example 1B herein;

DETAILED DESCRIPTION OF THE EXEMPLARY EMBODIMENT

Figure 1:
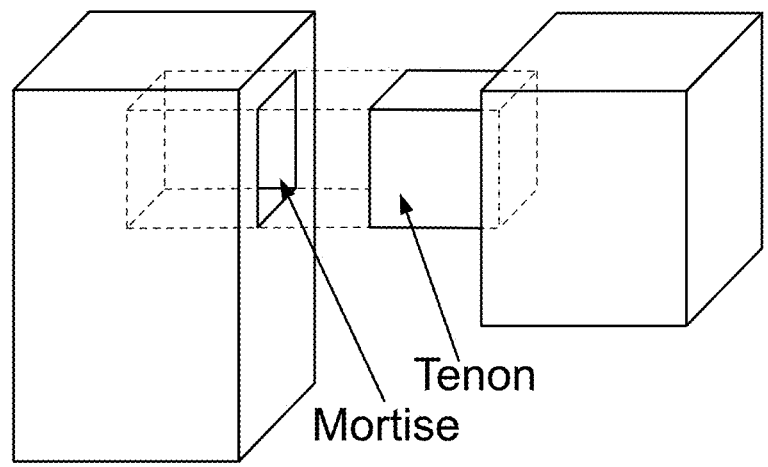
FIG. 1 is a schematic view showing the mortise and tenon technique for bone fixation.

The following disclosure is presented to provide an illustration of the general principles of the present invention and is not meant to limit, in any way, the inventive concepts contained herein. Moreover, the particular features described in this section can be used in combination with the other described features in each of the multitude of possible permutations and combinations contained herein.

All terms defined herein should be afforded their broadest possible interpretation, including any implied meanings as dictated by a reading of the specification as well as any words that a person having skill in the art and/or a dictionary, treatise, or similar authority would assign thereto.

Further, it should be noted that, as recited herein, the singular forms 'a,' "an," and "the" include the plural referents unless otherwise stated. Additionally, the terms "comprises" and "comprising" when used herein specify that certain features are present in that embodiment, however, this phrase should not be interpreted to preclude the presence or additional of additional steps, operations, features, components, and/or groups thereof.

The present disclosure generally relates to a surgically sized bone scaffold/implant that can sustain physiological loading and is suitable for cell and bone graft deposition to facilitate bone fusion in the long bone. A main advantage of the bone scaffold is its increased mechanical properties and biologically active capability.

In an embodiment, the scaffold is fabricated using biocompatible and biodegradable polylactic acid (PLA) material via 3D printing, providing new avenues for bone regeneration. Use of 3D printing provides opportunities for a variety of scaffold designs and configurations such as pore size, interconnected porosity, shape, and modulus may modified for different bone graft applications, whether it's used as filler for bone cancer resections or trauma, or as a fusion device in cases of surgery. Depending on the defect location of the bone shaft, the relative porosity of the scaffold may be modified to account for changes in cortical bone thickness.

As further discussed herein, the internal architecture of the scaffold includes a series of horizontal and vertical conduits to mimic the "plywood" anatomy of bone, which exhibits high mechanical strength but is low in weight. In one embodiment, the scaffold is made using approximately 6 grams of PLA filament and takes approximately two hours to fabricate, as compared to cadaveric donor (i.e., allograft) tissue which can take up to several days to process and prepare. Further, the scaffold incorporates different moduli to mimic characteristics of bone which accounts for both cancellous and cortical bone types. In one embodiment, the scaffold's design accounts for dissimilarities in bone morphology and comprises two appropriately located moduli which permit integration.

Polyactic Acid (PLA)

PLA is a nontoxic, biodegradable, and biocompatible resin that is that is derived from starches in foods, such as potatoes and corn. Being a bioresorbable polymer, PLA degrades via hydrolysis. While PLA is a biocompatible polymer suitable for medical implant applications, it is important to note that as it degrades it produces carboxylic acid chain ends that trigger decrease in local pH which can cause the body to develop an inflammatory response. The body's ability to tolerate this is dependent on whether it can excrete it to buffer the change and maintain homeostasis. Further, Meyer et al. examined the effects of lactic acid on human osteoblasts in vitro, it was found that too much lactic build up can interfere and inhibit the osteoblast proliferation and matrix mineralization. It would be helpful to investigate the cellular response with scaffolds that have been pre-degraded to various extents under in vitro conditions to carefully examine the effects of lactic acid. Assessment of wear generated from the scaffold may be measured in accordance to the ASTM 2025 standard, which utilizes a weight loss method for wear determination in polymeric components.

Eitenmuller et al. examined the use of bioresorbable PLLA screw and implants for the treatment of fractures in the foot and found that healing was achieved within 6 weeks, but 52% of the patients experienced aseptic soft tissue issues caused by the delayed clearance of degrading PLA particles. Alternatively, the same procedure was performed again utilizing reduced volume of material in the plates and screws, which addressed the soft tissue inflammatory reactions. This demonstrates that matching the degradation progress is critical for successful healing and the avoidance of adverse effects.

PLA undergoes bulk degradation via hydrolysis. Mass loss due to the dissolution of the polymer material results in changes to the scaffold's structural configuration as well as changes in mechanical properties such as compressive strength and stiffness. Hence, it is imperative that the degradation behavior of bioresorbable polymers such as PLA is better understood for implantable use, particularly with regards to monitoring the scaffold functionality as it degrades to ensure its long term biocompatibility is not compromised.

While PLA is preferred, other materials may be used in alternate embodiments of the scaffold. Examples of such materials include, without limitation, other biocompatible polymers, ceramics, metals (e.g., titanium and its alloys) and composite materials.

The scaffold of the present invention may be implanted in a similar fashion as compared to current techniques that are utilized today, such as the mortise and tenon technique, which has been utilized for the fixation of femurs and other long bones to bridge defects. Outside of medical applications, the mortise and tenon technique has been commonly used in woodworking to adjoin pieces of wood for thousands of years. The mortise and tenon concept is illustrated in FIG. 1.

Figure 2:
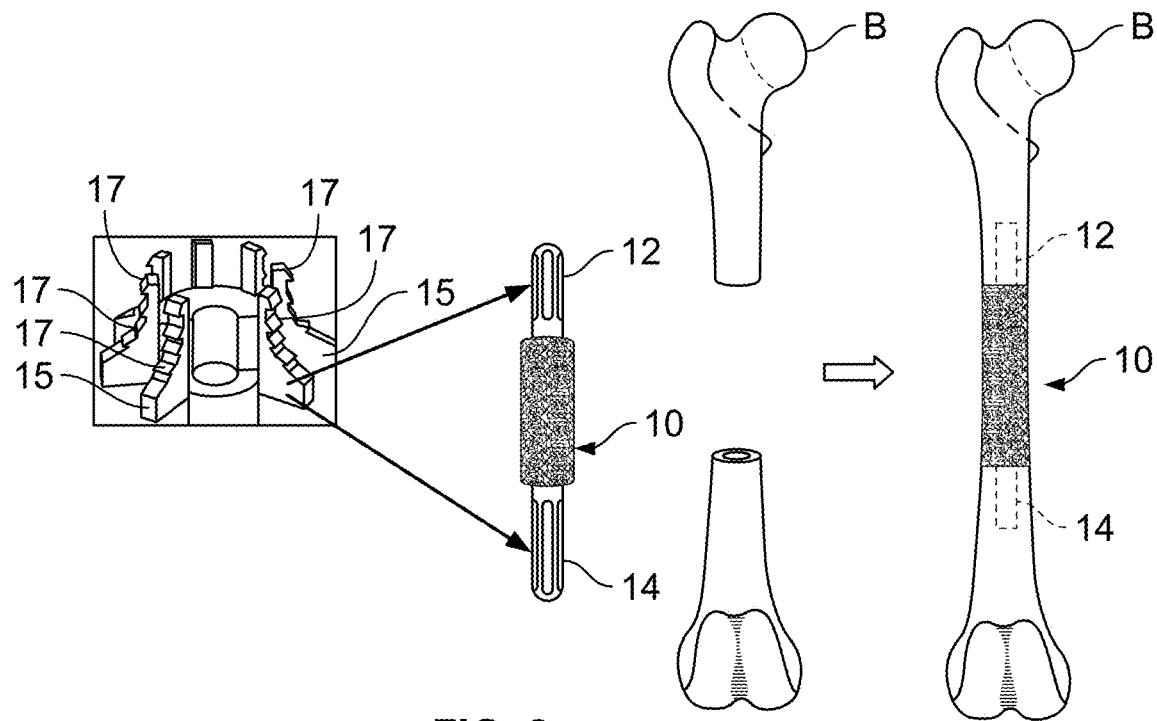
FIG. 2 is a schematic view of a scaffold according to an embodiment of the present invention, being used to repair a bone defect.

FIG. 2 illustrates an embodiment of the scaffold 10 of the present invention, as prepared and used clinically in cases of long bone reconstruction. In this embodiment, inserter guides 12, 14 are 3D printed on the top and bottom ends of the scaffold 10. Each of the inserter guides 12, 14 includes projections 15 having teeth 17 extending outward therefrom. When the inserter guides 12, 14 are inserted into a bone B, the teeth 17 engage the bone to secure the inserter guides 12, 14 therein, whereby the guides 12, 14 will lock and fixate the scaffold 10 into place within the bone B.

As metal plates and intramedullary nailing systems are traditionally used for the treatment of segmental bone repair procedures, it is generally advised to remove them once healing is complete to avoid osteopenia and soft tissue compromise. The surgical removal of internal fracture fixation systems has been reported as one of the most frequently performed orthopedic procedures in the western world, with the proximal femur, tibial shaft, and femoral shaft amongst the most common fracture cases. Infections, metal allergy, compromised wound healing, refracture, tissue damage, and bleeding are commonly observed complications following implant removal. In a clinical study involving 109 cases of femoral intramedullary nail removal, increased pain and discomfort was noted in over 20% of the patients post procedure. Use of this scaffold as an implant for the fusion of defects would not require removal as it is bioresorbable.

Immunological issues from harvesting cadaveric material, risk of infection, and surgical revision rates due to complication may be reduced by using biologically active, mechanically stable scaffolds. Thus, the ability to modify the geometries of the scaffold of the present invention in order to accommodate the size of bone graft reconstruction helps to eliminate the concerns of donor site availability, as scalability can be achieved through computer aided design software. The scaffold may be designed and formed so as to be patient-specific, based on the patient's MRI or CT scan provided by the physician.

Figure 4A:
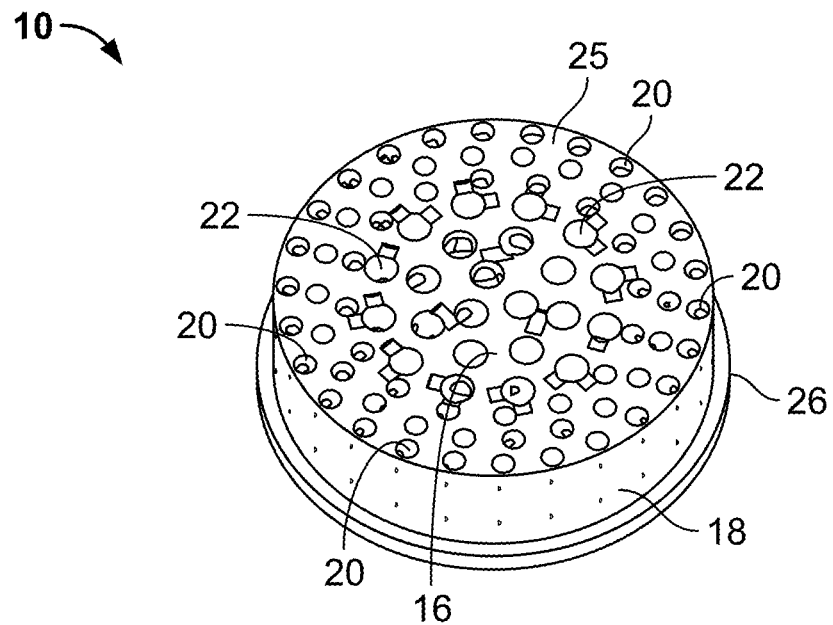
FIG. 4A is a top perspective view of a 3D-printed scaffold according to an embodiment of the present invention.
Figure 4B:
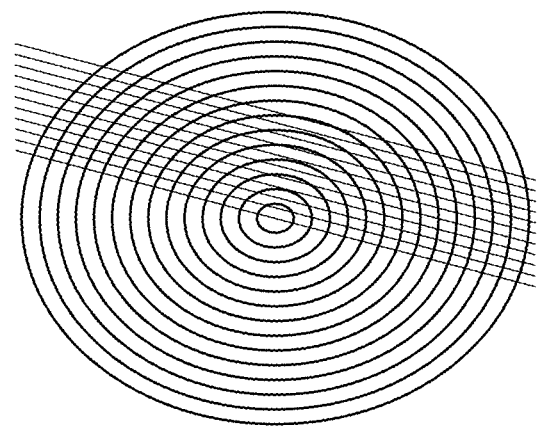
FIG. 4B is a set of concentric circles used as a footprint for 3D-printing the scaffold shown in FIG. 4A.

As further described herein, and illustrated in FIG. 4A, the scaffold 10 includes an inner core 16 and an outer core 18 that circumferentially engages the inner core 16. In other words, the outer core 18 includes, or constitutes, the periphery of the scaffold 10. Both the inner and outer cores 16, 18 exhibit characteristics comparable to native bone. The inner core 16 of the scaffold 10 possesses a relatively high level of porosity, thereby promoting increased flow for nutrients and molecules required to initiate and sustain osteointegration, while the outer core 18 of the scaffold 10 possesses a lower level of porosity relative to the inner core 16. This design results in an increased modulus in the outer core 18, which thereby provides a stable mechanical framework to minimize potential stress shielding, yet provides a platform for the onset of callus formation.

In an embodiment, the scaffold 10 is created using a 3D printer, such as those marketed under the Makerbot brand, loaded with a PLA filament. The scaffold 10 is first designed using three-dimensional design software, such as AutoCAD or SolidWorks, to create a desired shape with a desired porosity and a desired modulus size. The scaffold design is then presented to the 3D printer for fabrication. The 3D printer additively manufactures the scaffold 10, layer by layer (see Example 1 and FIGS. 12-13B). FIGS. 4A, 5A, 5B, 14A and 14B show examples of such 3D-printed scaffolds. FIG. 4D is a set of concentric circles used as a footprint for 3D-printing the scaffold 10.

In an embodiment of the scaffold 10, the diameter of the inner core 16 is 20 mm and the diameter of the outer core 18 is 30 mm. The height of the scaffold 10 is 8 mm. The scaffold 10 has spherical pores 20 (see FIGS. 4A and 14A) in its upper (i.e., superior) surface 25, each having a diameter of 300 microns. The upper surface 25 of the scaffold 10 may also have a second set of pores 22 having a different (e.g., larger) diameter (see FIGS. 4A and 14A) and/or pores having a non-spherical shape 24 (see FIG. 5A). In other embodiments, the scaffold architecture (properties, shape, and dimensions) is customized to accommodate the bone defect site.

In an embodiment, the scaffold 10 may also include a base plate 26 (see FIGS. 4A, 5A and 5B) on the surface opposite the upper surface 25. The base plate 26 may be used to trap and contain grafting materials (e.g., allograft bone, autograft bone, etc.).

Limb salvage surgery for osteosarcomas is a complex procedure because the operation entails removing tumor tissues but leaving the limb intact and preserving its function as much as possible. Additionally, the risk of infection for graft/prosthesis failure poses a major challenge in which 25% of the time revision surgery or amputation is required.

Traditionally, limb reconstruction involving allografting was the common method, until use of fibula flaps (autografting) was introduced in the mid-1970's. Studies have reported 12% post-operative infections and 78% uncomplicated bone union rates, both of which are improved results compared to the traditional allograft reconstruction. However, fibula harvesting has limitations, as 4-6 cm of the fibular bone must be preserved to minimize risk of complications. Studies have also reported success rates in combined use of bone allograft and vascularized fibula for reconstruction of large segmental bone defects. Known as the Capanna technique, the biological profiles of vascularized fibula and a structural allograft serve to complement each other based on structural integrity provided by the allograft and osteogenic capabilities provided by the autograft. Despite decreased infection rates in this technique (8.5% in tibial reconstructions, 6% in femoral reconstructions), the Capanna technique is limited to defects that are smaller than 5 cm. The limitations with traditional methods may be overcome through use of the scaffold of the present invention.

Figure 3:
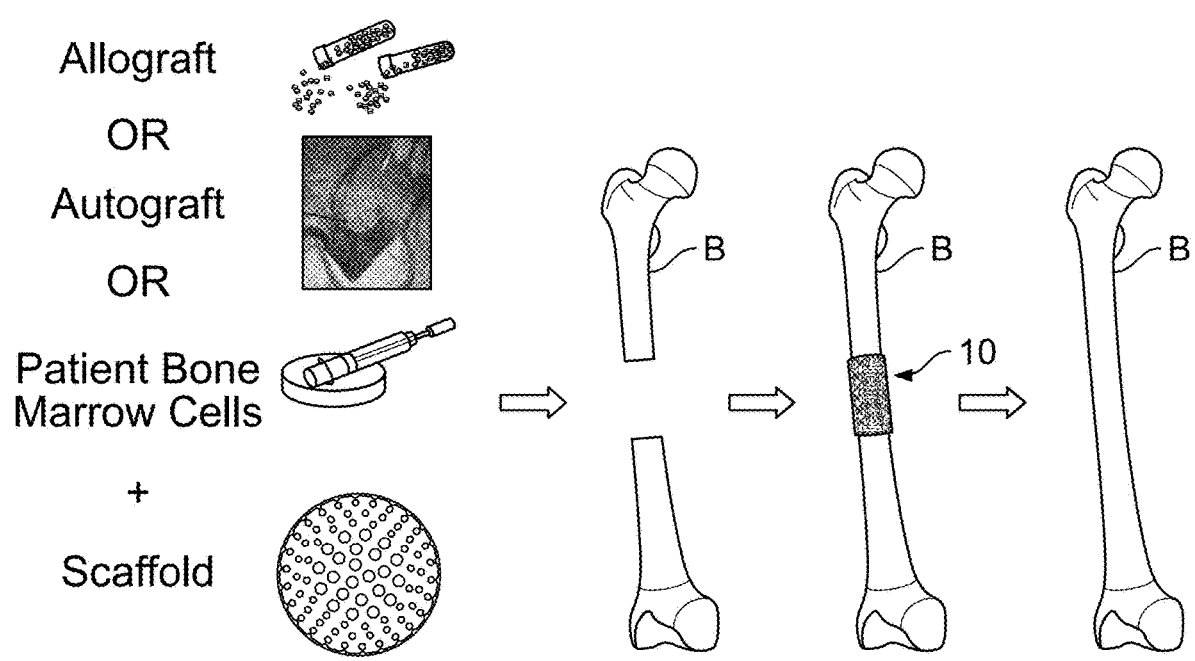
FIG. 3 is a schematic view of potential clinical applications of the scaffold of FIG. 2 in segmental bone replacement procedures.

In a bone grafting procedure, the physician will make an incision through the patient's skin covering the area in need of repair. Any scar, dead and/or tumorous tissue will be removed. The patient's bone will be reconstructed using a bone graft. Overall, bone graft material may include autograft bone, allograft bone, autograft bone and/or patient bone marrow cells, allograft bone and patient bone marrow cells, or, according to embodiments of the present invention, the scaffold and autograft bone, the scaffold and allograft bone, and/or the scaffold and patient bone marrow cells. Such clinical applications of the scaffold 10 in segmental bone replacement procedures are illustrated in FIG. 3. As an example, a clinician may obtain a biopsy of a patient's own bone marrow cells, culture and seed these cells onto the scaffold in vitro, and implant the scaffold/tissue construct into the patient's body. Incorporating the use of the scaffold, in whichever allograft bone/autograft bone/bone marrow cells combination, reduces the quantity of cadaveric donor tissue needed and wait time to process and prepare the graft for surgery.

The use of allograft bone or autograft bone is a decision made by the surgeon, based at least on the clinical condition of the patient. The physical state of the allograft bone or autograft bone is also the surgeon's decision, based on at least on the clinical condition of the patient. More particularly, the allograft bone or autograft bone may be solid, made into chips or fragments, or combined with liquid material(s) such as blood and ground into a paste. Regardless of its physical state, the allograft bone or autograft bone is, in an embodiment, placed on the upper surface 25 of the scaffold 10 (e.g., see FIGS. 4A, 5A, 5B, 14A, 14B, 18A and 18B), and the combination of scaffold and graft is then implanted (e.g., press fit) into the patient's bone defect. If in a non-solid physical state (e.g., into chips, fragments, or a paste, as described above), the allograft bone or autograft bone may be inserted into the pores 20, 22 of the scaffold 10, whereupon it may flow through vertical conduits 70 formed in the scaffold 10 (as described herein). The base 26 of the scaffold 10 may be removed to allow for additional flow, if warranted.

The scaffold is clinically applicable for bone grafting incorporation by providing structural mechanical stability to withstand load-bearing conditions. As discussed in the Examples below, the scaffold was subjected to a series of static and dynamic mechanical testing for design validation. Results of these tests revealed the compressive failure rate of the scaffold to be 9600N, which is 1.25× (i.e., 1.25 times) that of an adult human femur, which is the longest and strongest bone in the body. Its compressive stiffness was found to be 16650 N/mm, which is 6.3× (i.e., 6.3 times) that of adult human femur. Possessing characteristics stronger than the native bone tissue is ideal as the scaffold degrades over time as bone cells proliferate to achieve fusion. In one embodiment, the scaffold degrades in a controlled fashion without losing its mechanical integrity, and leave behind a newly regenerated bone tissue. Further such superior properties of the scaffold suggest that perhaps no external fixation would be needed to supplement bone graft procedures.

Figure 5A:
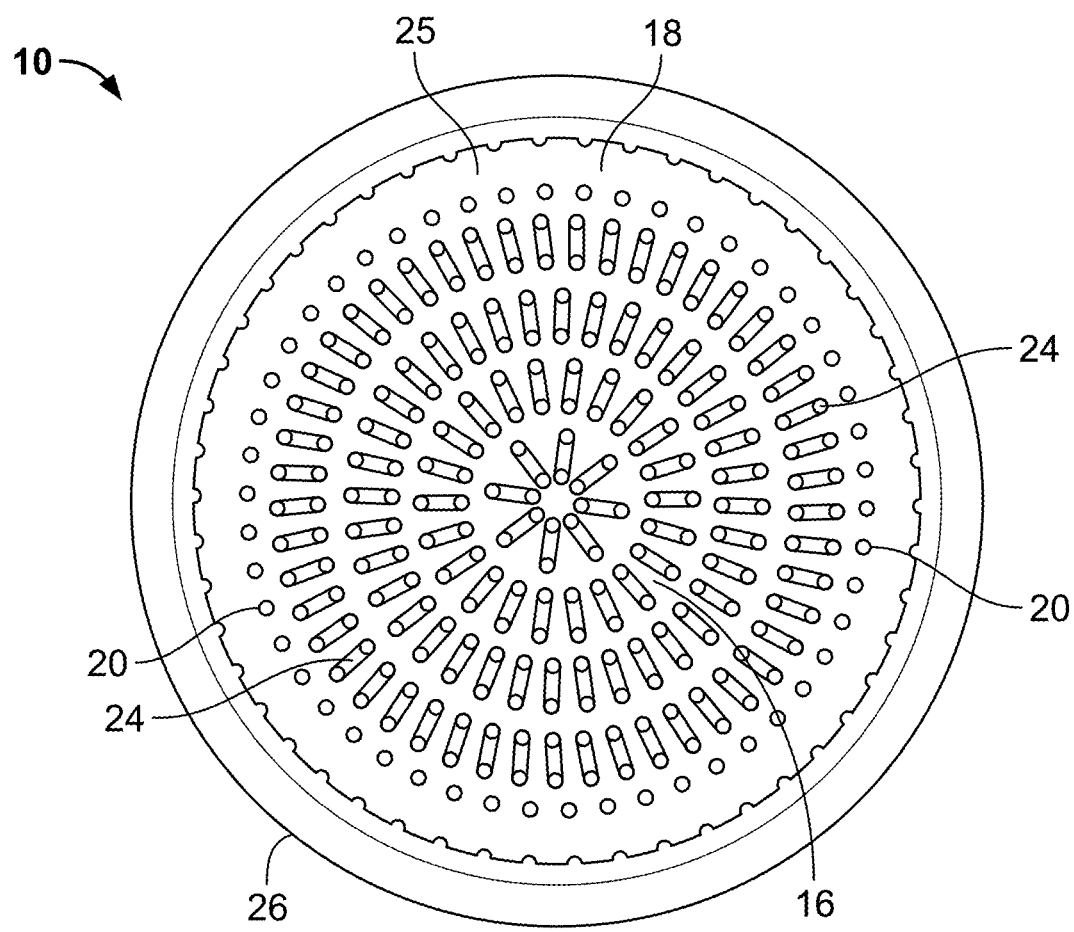
FIG. 5A is a top plan view of a scaffold according to an embodiment of the present invention.
Figure 5B:
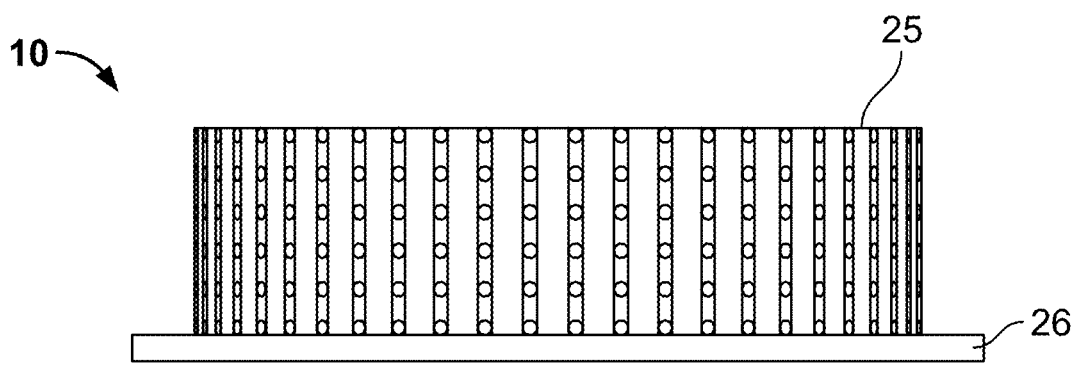
FIG. 5B is a side elevational view of the scaffold shown in FIG. 5A.
Figure 6:
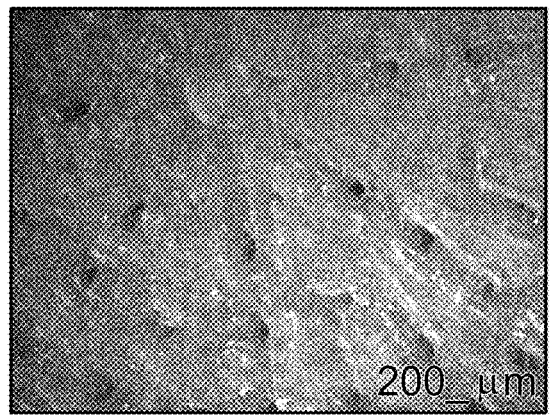
FIG. 6 is a photograph of a stereoscopic view of the scaffold shown in FIG. 5A, focusing on the boundary between the inner core and the outer core of the scaffold, the view having a magnification of 0.75×.
Figure 7:
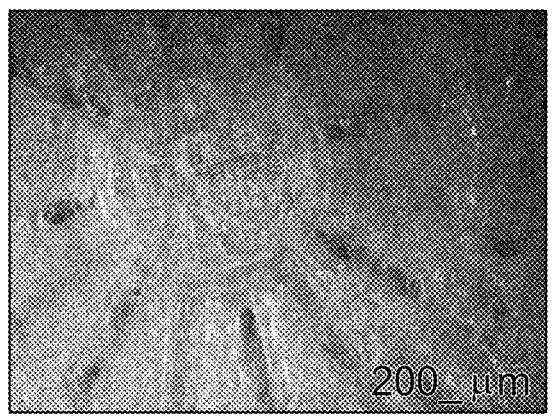
FIG. 7 is a photograph of a stereoscopic view of the scaffold shown in FIG. 5A focusing on the boundary between the inner core and the outer core of the scaffold, the view having a magnification of 0.75×.
Figure 8:
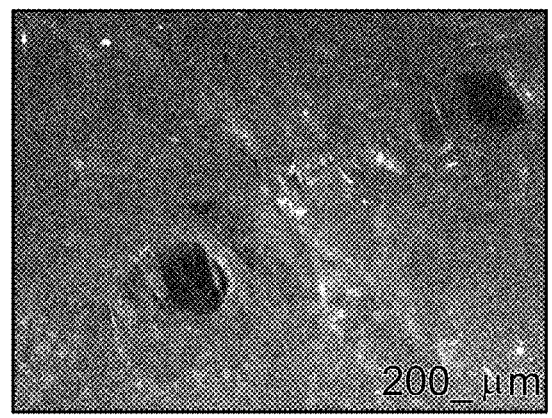
FIG. 8 is a photograph of a stereoscopic view of the scaffold shown in FIG. 5A focusing on the boundary between the inner core and the outer core of the scaffold, the view having a magnification of 3×.
Figure 9:
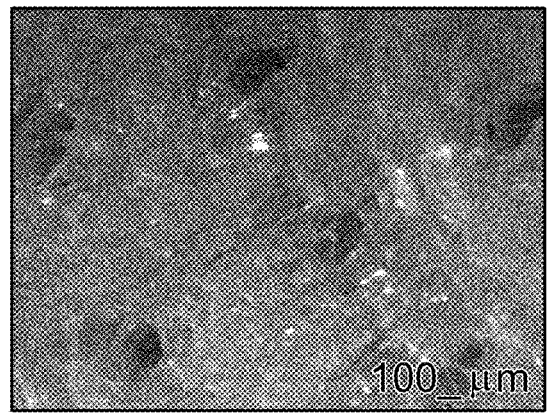
FIG. 9 is a photograph of a stereoscopic view of the scaffold shown in FIG. 5A focusing on the boundary between the inner core and the outer core of the scaffold, the view having a magnification of 2×.
Figure 10:
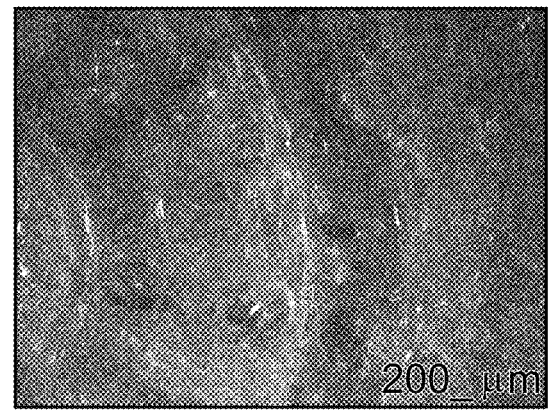
FIG. 10 is a photograph of a stereoscopic view of the scaffold shown in FIG. 5A focusing on the boundary between the inner core and the outer core of the scaffold, the view having a magnification of 1×.
Figure 11:
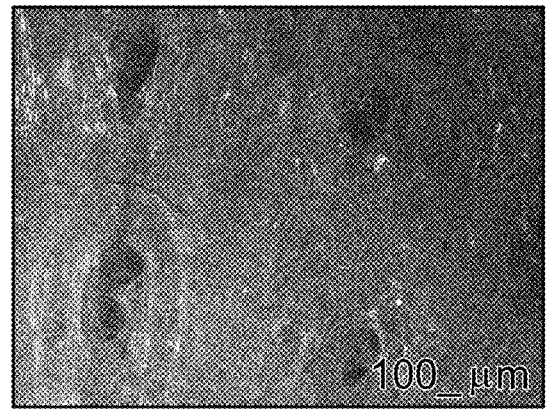
FIG. 11 is a photograph of a stereoscopic view of the scaffold shown in FIG. 5A focusing on the boundary between the inner core and the outer core of the scaffold, the view having a magnification of 2×.

FIGS. 6-11 are photographs of the scaffold 10 shown in FIGS. 5A and 5B, as taken using a camera connected to a stereomicroscope at various magnifications. Measurements of the pore geometries of all regions of the scaffold 10 were quantified to confirm consistency between prints. Based on qualitative analysis, there is a clear distinction between the inner core 16 and outer core 18 boundary based on changes in porosity between the interior and exterior regions.

The below Examples reveal data regarding testing of the scaffold's static mechanical properties, fatigue characteristics, and regional dynamic mechanical performance, as well as cell migration patterns when the scaffold is seeded with cells.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for.

Example 1A

Scaffold Fabrication

Figure 12:
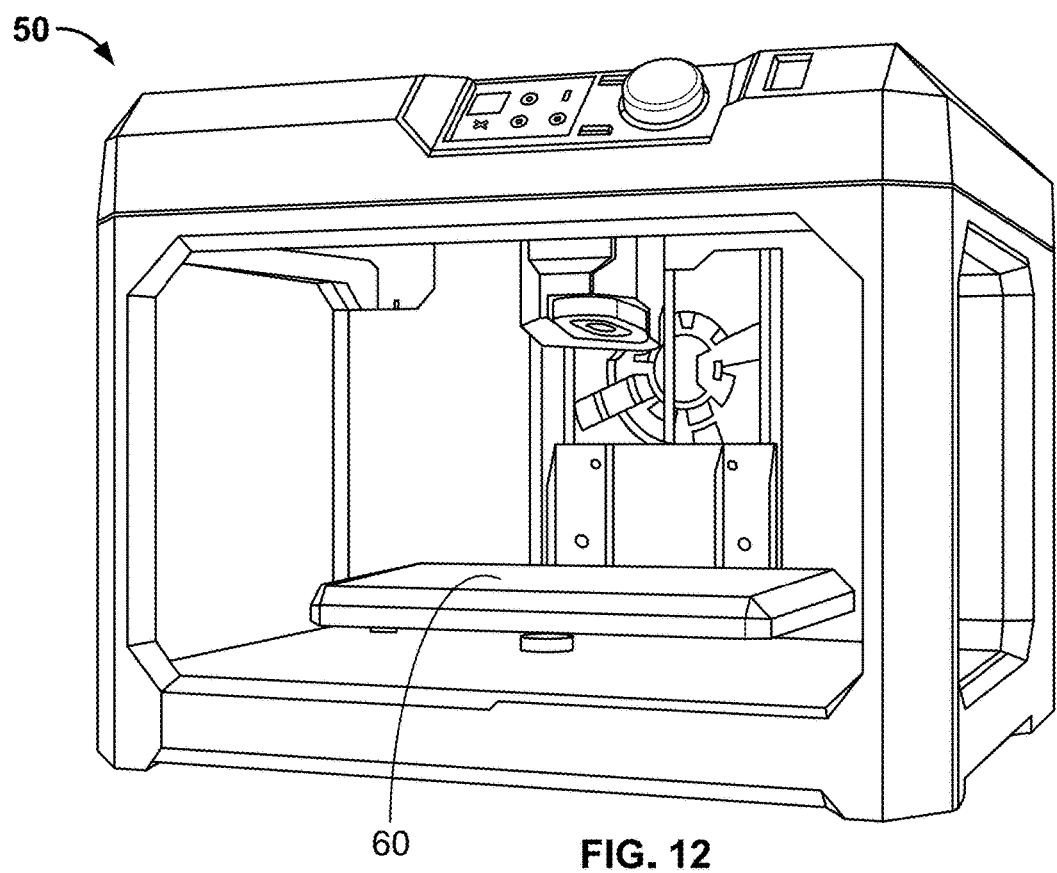
FIG. 12 is a perspective view of a 3D printer used to fabricate the scaffold shown in FIG. 5A, as discussed in Example 1A herein.
Figure 13A:
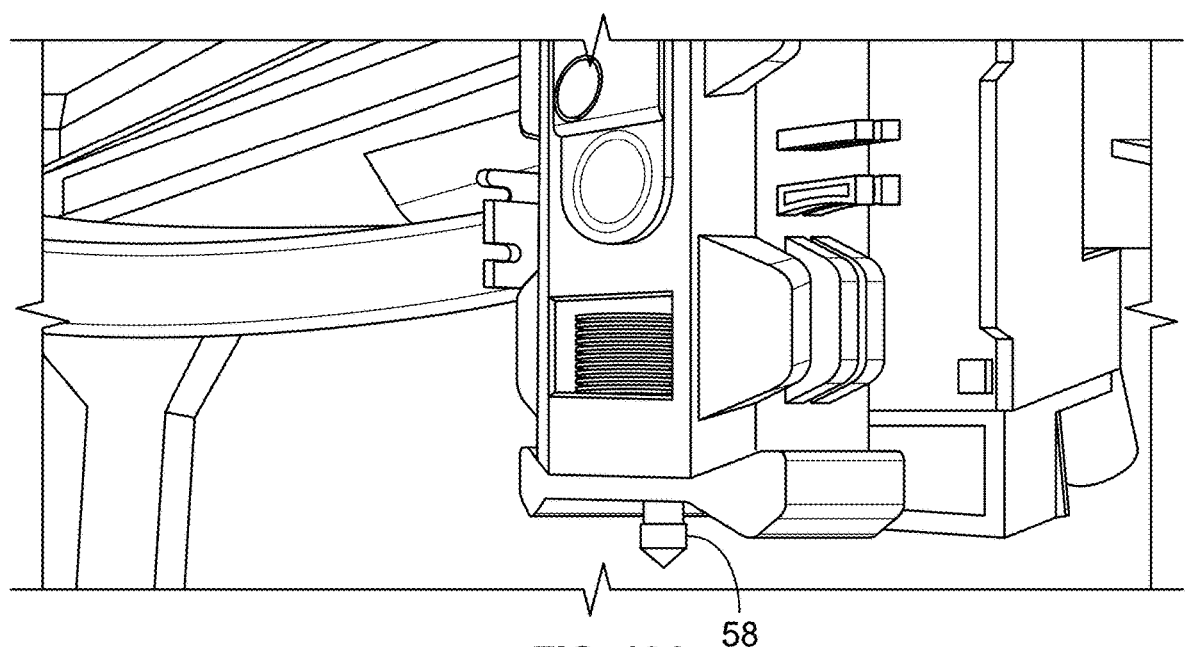
FIG. 13A is a detailed view of the 3D printer shown in FIG. 12, showing the extruder nozzle thereof, as discussed in Example 1A herein.
Figure 13B:
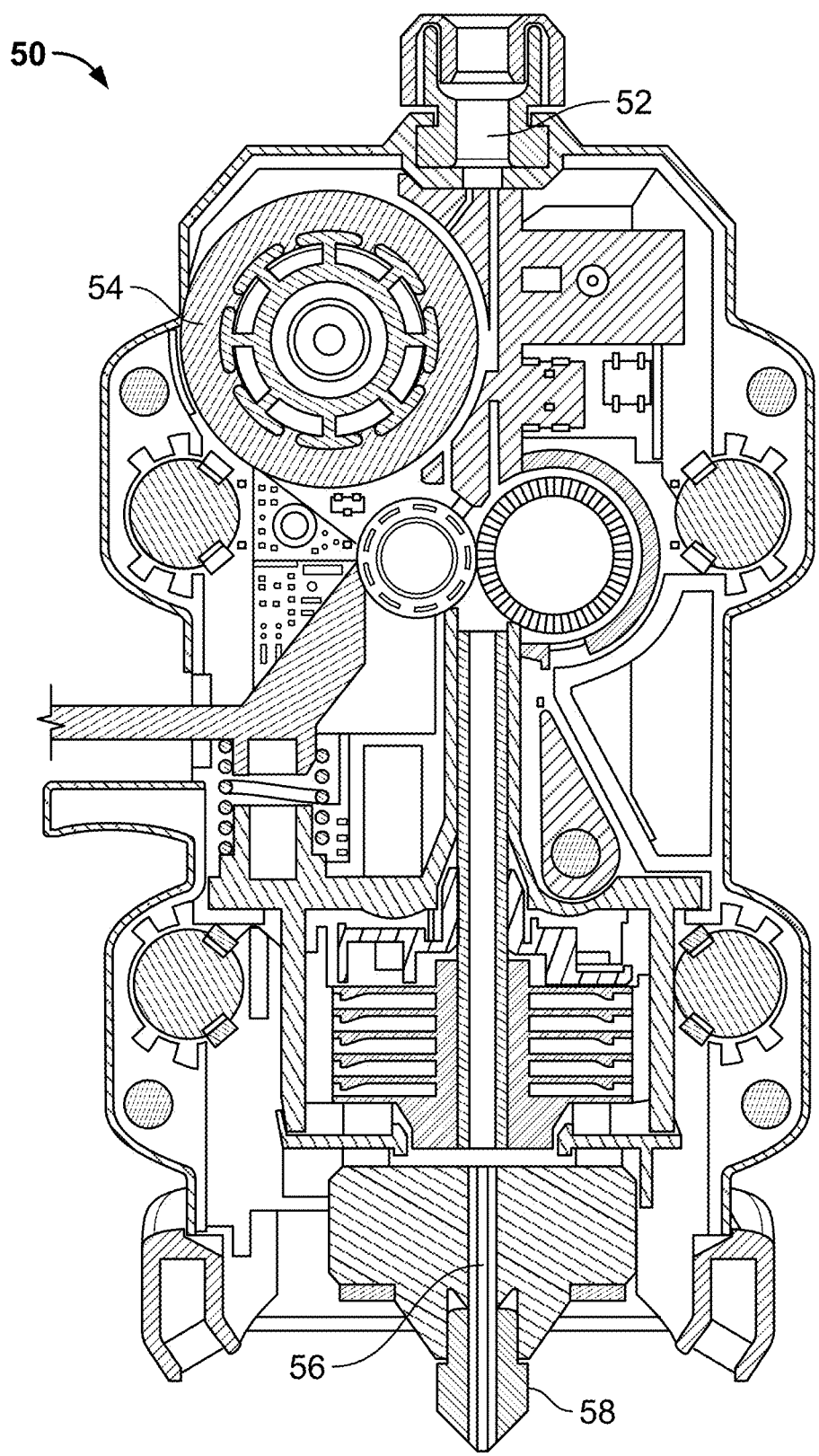
FIG. 13B is a cross-sectional view of the 3D printer shown in FIG. 12, as discussed in Example 1 herein.

A Makerbot Replicator 5th Generation 3D printer 50 was used to fabricate scaffold prototypes (see FIGS. 12 and 13A-B). The scaffold is preferably made of polylactic acid (PLA), a bioresorbable polymer, which does not require removal after implantation into a patient. The spool of PLA filament (Makerbot, Brooklyn N.Y.) (not shown) is inserted into the filament loader/unloader 52 and pulled by an encoder wheel 54 which moves filament along in small increments as printing progresses. Use of a gear through the print head of the printer 50 facilitates continuous fabrication. The PLA filament is liquefied in the heated tube 56 and extruded through the pointed extruder nozzle 58 in ultra-fine lines (e.g., having a width of 0.1 mm) and quickly solidifies as it reaches the build plate 60 for form a layer (not shown). This process repeats, printing layer by layer and sealing the layers together, until the scaffold 10 is complete.

The prototype scaffold 10 is shown in FIGS. 14A and 14B, and was printed at a layer resolution of 0.10 mm, infill density at 100%, and infill layer height at 0.10 mm. Approximately 8 grams of PLA filament and two and a half hours is required to fabricate the scaffold, as compared to cadaveric donor tissue preparation time, which can take up to several days, even weeks, to process and prepare. Further, as a 0.9 kg spool of PLA filament costs $48.00, each prototype scaffold 10 only costs $0.43 to fabricate. In comparison, metal fixation systems such as intramedullary devices cost approximately $95.00 for the nail and $15.00 for each interlocking screw used, and typically more than one screw is required to secure the nail. Further, intramedullary devices are subsequently removed months after implantation, and these procedures have been reported to cost $14,000, not including the ancillary costs such as absence from the workplace and pain medications.

One of the greatest challenges with metal orthopedic implants is the issue of stress shielding, as traditionally fabricated metal implants are much stronger and stiffer than native bone into/adjacent to which they are implanted. As a result, the insufficient load transfer to the patient's bone causes bone resorption as stress is not detected, possibly leading to increased risk of implant failure.

Therefore, use of 3D printing for the fabrication of scaffolds facilitates variations in designs and configurations: pore size, interconnected porosity, shape, and modulus may modified accordingly based on different bone graft applications, such as a filler for bone cancer resections or trauma, or as a fusion device in cases of surgery. The scaffolds may be fabricated to suit the patient's bone defect. The cross-sectional geometry and thickness of the scaffold varies, depending on where it is placed within the patient's bone. Depending on the defect location, the relative porosity of the scaffold may be modified to account for changes in cortical bone thickness, as shown in FIG. 15. Three scaffolds A, B and C having different relative porosities are shown. More particularly, scaffolds A, B, C are examples of three variations of scaffold configurations which may be suited for the metaphysis, epiphysis, and diaphysis regions, respectively, along the long bone.

The fabrication of load-sustaining scaffolds may alleviate the need for use of metal fixation systems typically used to provide enhanced stability and support of graft sites following reconstruction procedures.

Example 1B

Scaffold Design

Figure 16A:
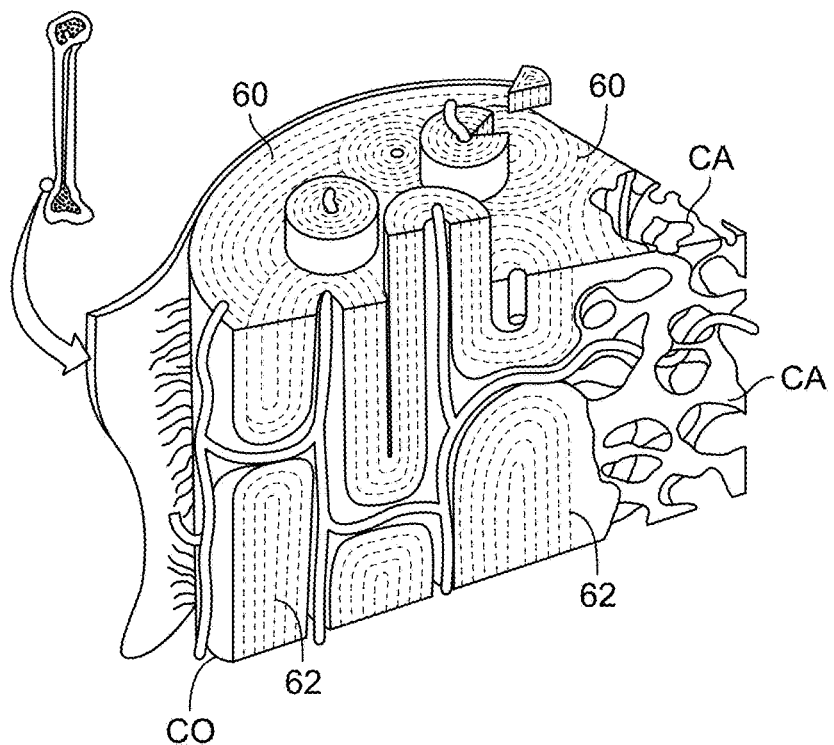
FIG. 16A is a sectional schematic view of a long bone.
Figure 16B:
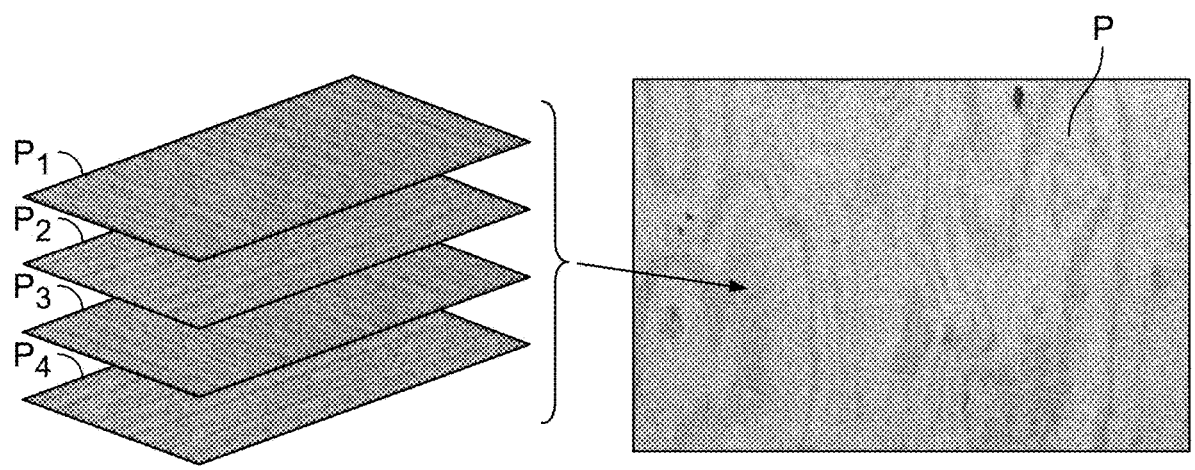
FIG. 16B is an exploded schematic view of a piece of plywood.

Referring now to FIG. 16A, long bones include both cortical bone CO and cancellous bone CA. The internal structure of bone includes a series of horizontal and vertical conduits 60, 62, respectively, which are arranged in an alternating fashion. This arrangement is similar to plywood P (see FIG. 16B), which is made up of thin layers of wood $P_1$, $P_2$, $P_3$ and $P_4$ sealed together with alternating grain orientation, which make it strong in all directions.

Like natural bone, the internal architecture of the scaffold 10, as shown in FIG. 17, includes a series of alternating vertical and horizontal conduits 70, 72, respectively, that mimic the plywood-like anatomy of bone, thereby exhibiting high mechanical strength while having low weight. FIG. 18A shows the entire scaffold 10, while FIG. 18B is a sectional cutaway view of the scaffold 10, wherein the vertical and horizontal conduits 70, 72 are visible. In various embodiments, the vertical and horizontal conduits 70, 72 may have cross sections with different geometries, including, but not limited to, spherical, circular and hexagonal. In an embodiment, at least some of the vertical and horizontal conduits 70, 72 are be non-linear, and thereby constitute a maze-like structure within the scaffold 10. In an embodiment, at least some of the vertical conduits 70 are continuous with the pores 20, 22 defined by the surface 25 of the scaffold 10.

The prototype scaffold 10 shown in FIGS. 18A-B has a 32.00 mm diameter and a 9.5 mm height. The printed scaffolds 10 (N=50) measure 31.87±0.08 mm diameter and 9.59±0.23 mm in height, resulting in a 0.8% and 0.7% coefficient of variation for diameter and height, respectively. This demonstrates that 3D printing may be a reproducible method for fabrication of scaffolds. Further, the scaffold of the present invention incorporates different moduli to mimic characteristics of bone, which accounts for both cancellous and cortical bone types. The difference in moduli is achieved by gradually decreasing the size of the vertical conduits 70 and the size of the horizontal conduits 72 from the inner core 16 toward the outer core 18 of the scaffold 10. This design results in more material being present at the outer core 18, thereby increasing its strength, and emulating the internal architecture of natural bone.

The vertical and horizontal conduits $70_I$, $72_I$ in the inner core 16 of the scaffold 10 measure 2 mm diameter×2 mm height and 0.825 mm diameter×2 mm length, respectively. The vertical and horizontal conduits $70_O$, $72_O$ in the outer core 18 of the scaffold 10 measure 1.5 mm diameter×2 mm height and 0.625 mm diameter×1.5 mm length, respectively.

Accounting for dissimilarities in bone morphology is essential and the advantages of a modulus-matched implant are substantial. In the case of an implant-bone interface, the sharp change in modulus can increase the risk of failure and fracture. A functionally-graded scaffold having two appropriately located moduli would be more effective in permitting integration in the patient's bone. Referring again to FIG. 18B, the inner core 16 of the scaffold 10 possesses increased porosity by having larger vertical and horizontal conduits $70_I$, $72_I$ (i.e., relative to the size of the vertical and horizontal conduits $70_O$, $72_O$ of the outer core 18), thereby promoting increased flow for nutrients and molecules required to initiate and sustain osteointegration. The outer core 18 of the scaffold 10 has decreased porosity relative to the inner core 16 due to its relatively smaller vertical and horizontal conduits $70_O$, $72_O$. The resulting greater modulus of the outer core 18 thus provides a stable mechanical framework to minimize potential stress shielding yet offers a platform for the onset of callus formation.

Figure 19:
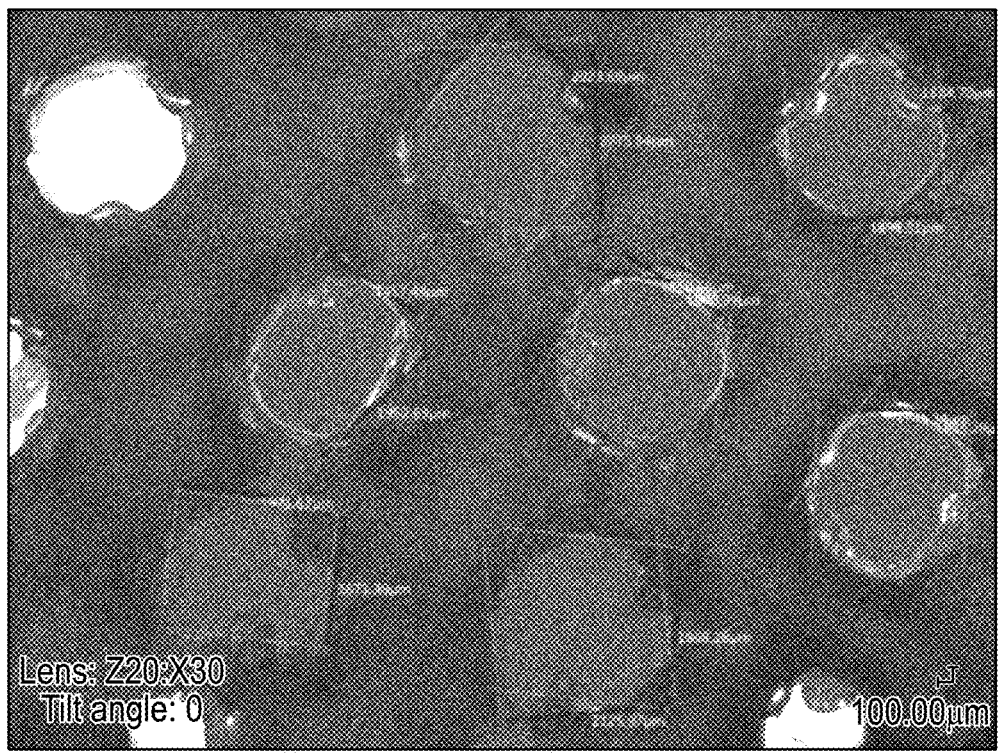
FIG. 19 is a set of photographs of a stereoscopic view of the scaffold shown in FIGS. 18A and 18B with the scaffold's inner core shown in the top image, and the scaffold's outer core shown in the bottom image, both taken at 30× magnification, as discussed in Example 1B herein.
Figure 19:
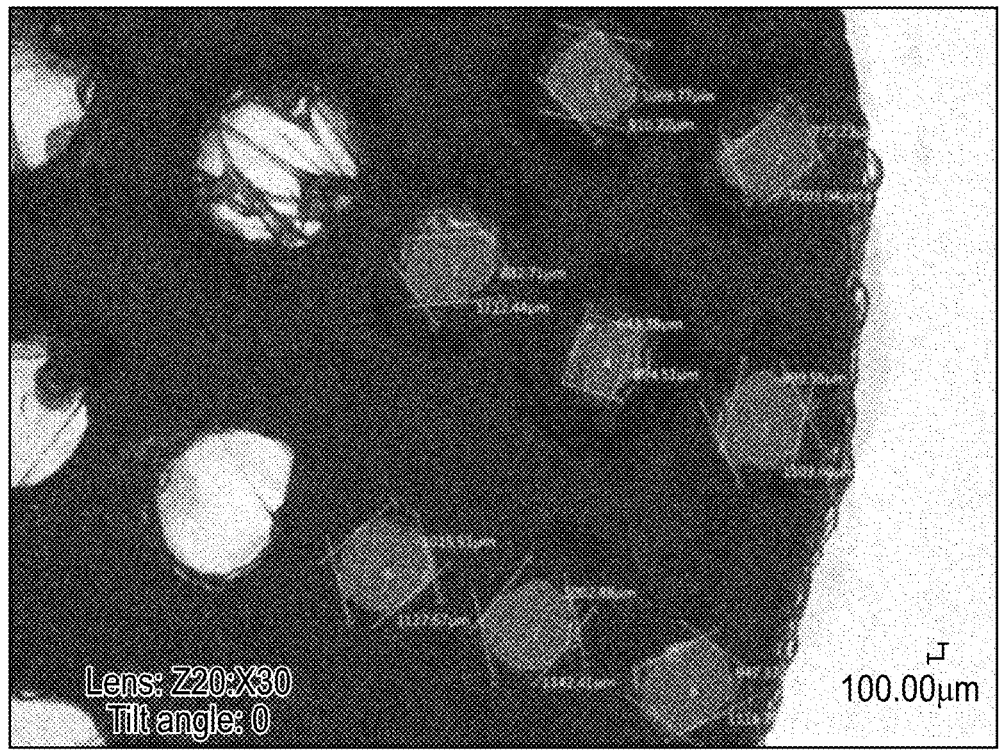

The scaffolds were examined under the microscope after being 3D-printed to evaluate quality and consistency between prints. The pore sizes in the inner and outer cores of the scaffold were measured using a VHX-5000 Digital Microscope (Keyence, Itasca, Ill.) prior to assigning scaffolds to static and dynamic mechanical testing in a randomized fashion. The capability of the microscope enabled pore sizes in the inner and outer cores to be measured. As shown in the microscopic image of FIG. 19, the average pore size of the inner core 16 is 1880±133 μm (top image) and the average pore size of the outer core 18 is 980±56 μm (bottom image).

Example 1C

Mechanical Testing: Static Analysis

Figure 20:
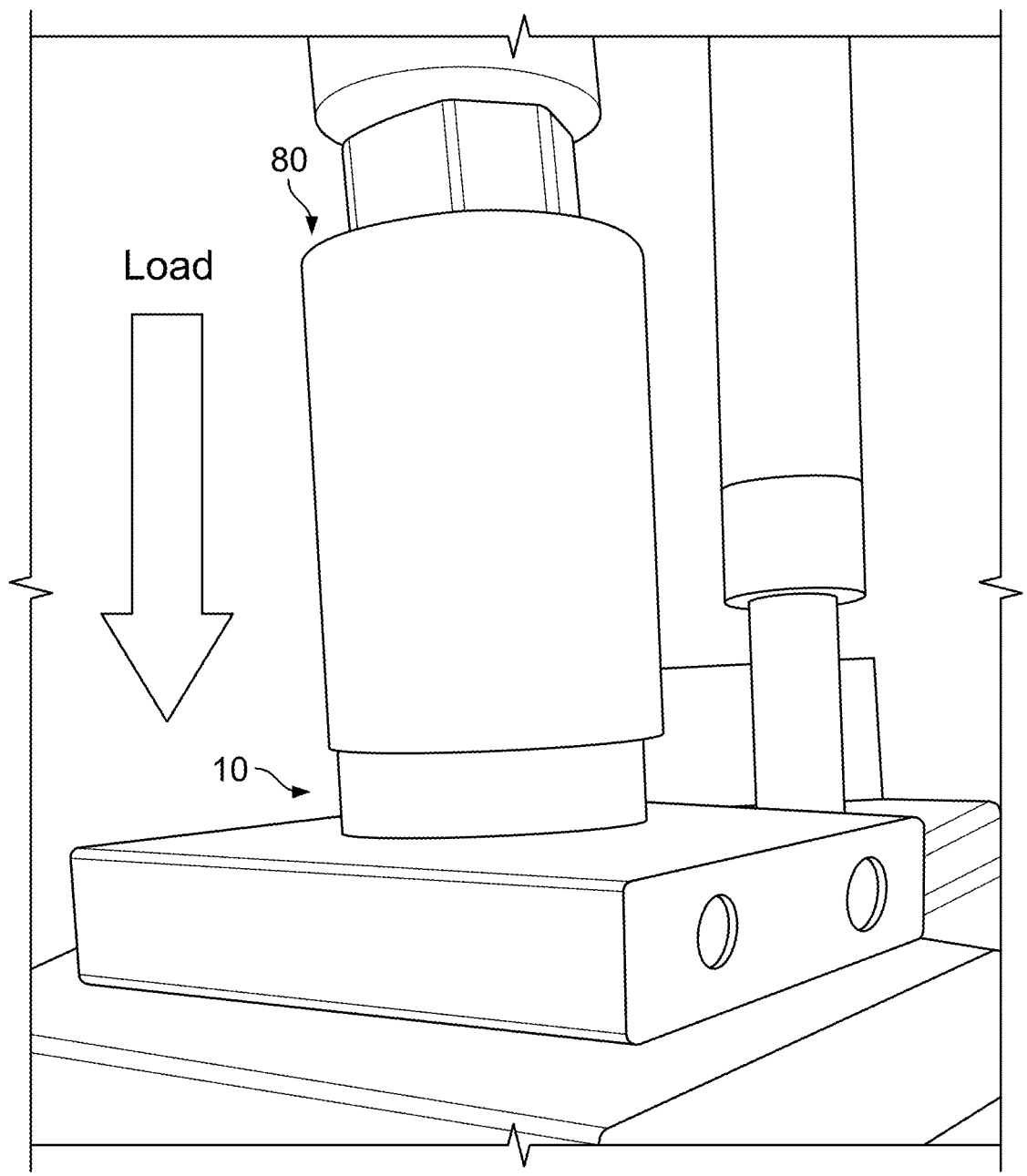
FIG. 20 is a schematic view of an experimental testing setup showing a scaffold according to an embodiment of the present invention, as aligned with the loading axis of a materials testing machine, as discussed in Example 1C herein.

To determine its static mechanical properties, the scaffold 10 (N=5) was aligned with the loading axis of a MTS 858 Bionix Testing Machine 80 (MTS, Eden Prairie, Minn.) and loaded to failure in displacement control at a rate of 25 mm/min while continuously acquiring load versus displacement data at a sampling rate of 40 Hz (see FIG. 20). Load versus displacement curves for each scaffold 10 were recoded and analyzed to determine the failure load and stiffness. A one sample t-test comparison between experimental findings with (upper) mean literature values was performed to detect for any statistical differences. A p-value less than 0.05 was used to indicate statistical significance.

Figure 21:
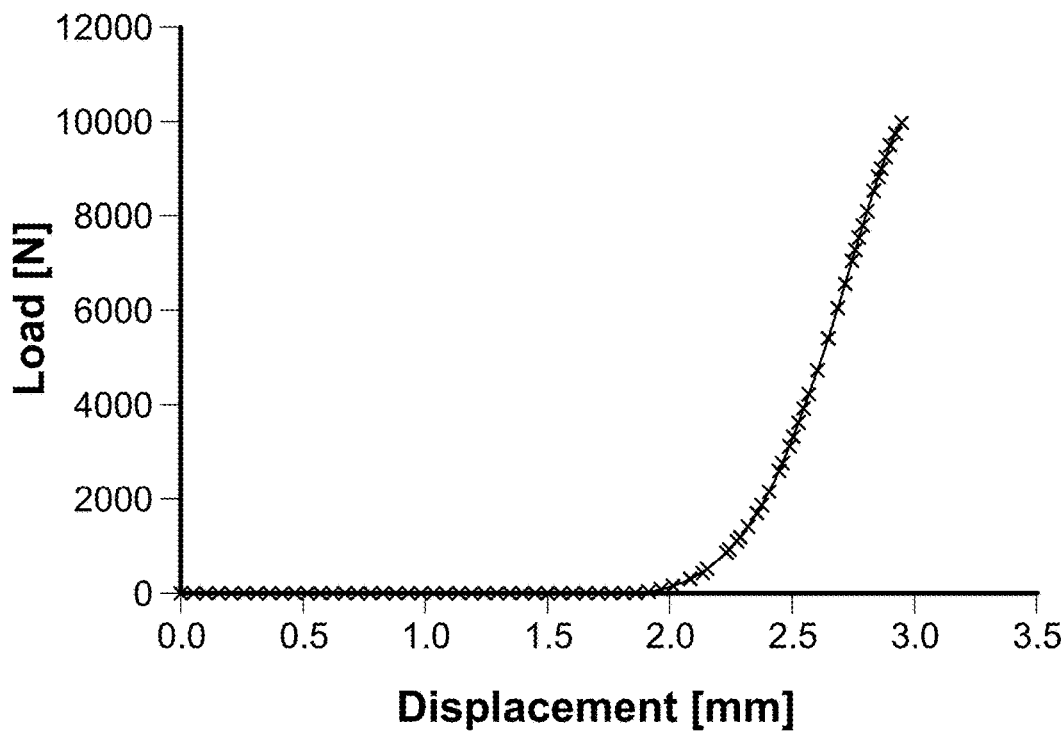
FIG. 21 is a Typical Load vs. Displacement curve generated from static testing of the scaffold shown in FIG. 20.

A one sample t-test comparison between experimental findings from the literature for femur failure load and stiffness revealed no significant differences regarding stiffness ($p>0.05$) and a statistically higher failure load for the scaffold ($p<0.001$). The average failure load and stiffness was calculated based on the load versus deformation curve generated from the static test (see FIG. 21), and the results are set out in Table 1. The average failure load of the scaffold was found to be 9645±54 N, which is comparable to adult human femurs 7620 N to 9076 N, (depending on the testing configuration). Based on the failure load and surface area of the scaffold, the ultimate stress was calculated to be 34.2 MPa. Further, in comparison to the average stiffness of human femurs which have been reported to be 2924 N/mm to 4033 N/mm (depending on the testing configuration), the stiffness of the scaffold was also comparable at 4025±304 N/mm. This is ideal since PLA is a biodegradable polymer that has a degradation lifespan of 1-2 years. The scaffold will degrade slowly as bone cells proliferate and mineralize to heal while still maintaining the required structural and mechanical integrity to withstand physiological weight bearing loads.

TABLE 1

Results of static test on scaffold showing failure load, and stiffness calculated from the load versus displacement curves for each scaffold

|  | Scaffold (N = 5) | Comparison to Adult Human Femur |
|---|---|---|
| Average Failure Load at | (9645 ± 54)N | 7620N to 9076N |
| Average Stiffness at | (4025 ± 304)N/mm | 2924N/mm to 4033N/mm |

Figure 22:
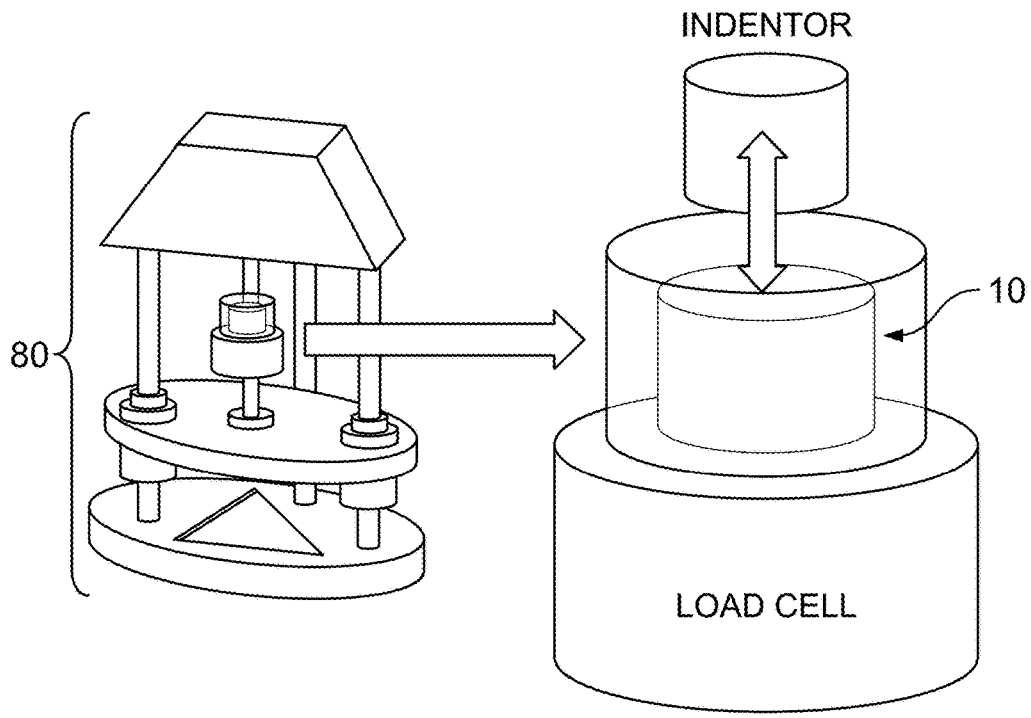
FIG. 22 is a schematic view of an experimental test setup including a scaffold according to an embodiment of the present invention or specimen, as aligned with the loading axis of a materials testing machine, as discussed in Example 1C herein.

Six samples of the 3D printed scaffolds 10 were tested under cyclic deformation using a materials' testing machine 80 (Bose ELF3200, Eden Prairie, Minn.), as shown in FIG. 22. Samples were immersed in High Performance Cell Culture Media (RoosterBio, Frederick, Md.) 15 minutes prior to loading. Compressive sinusoidal fatigue loading was applied from −5N to −50N for 535 cycles. Continuous load vs. deformation data was acquired beginning at cycle number 10 and at subsequent 25 cycle intervals thereafter. Deformation change at each cycle count was computed, averaged across each cycle count, and subjected to nonlinear analysis (Prism 5.0, GraphPad Inc., San Diego, Calif.). The nonlinear exponential regression produced the parameter K the rate constant, expressed in reciprocal of the X axis units (Cycles−1) and is related to the rate at which the deformation value changes over the number of cycles. Trabecular bone specimens were obtained by extracting the central core of thirty frozen thoracic (T9, T10, T11) vertebral bodies of 100 kg porcine (Animal Technologies Inc., Tyler, Tex.) using a 10 mm diameter trephine. These specimens were milled to achieve a height of 10 mm and flat surface for loading, and were subjected to identical loading conditions and analysis previously described.

Figure 23A:
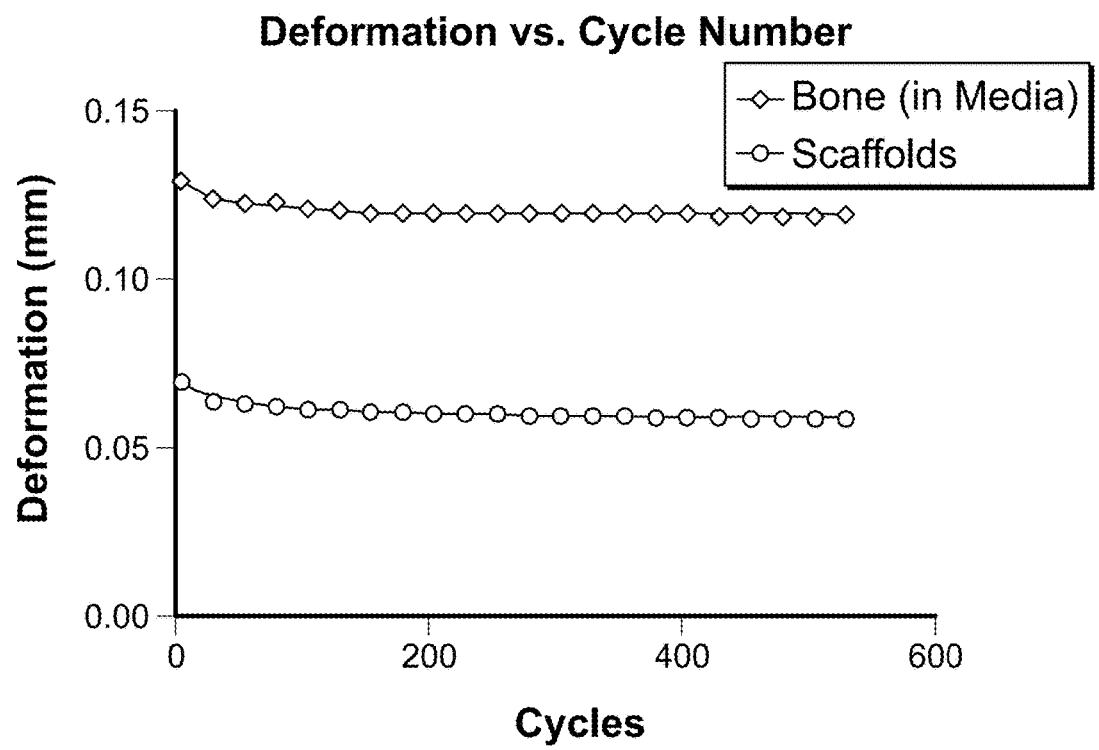
FIG. 23A is a curve showing deformation versus cycle number, as generated from static testing of the scaffold shown in FIG. 22.
Figure 23B:
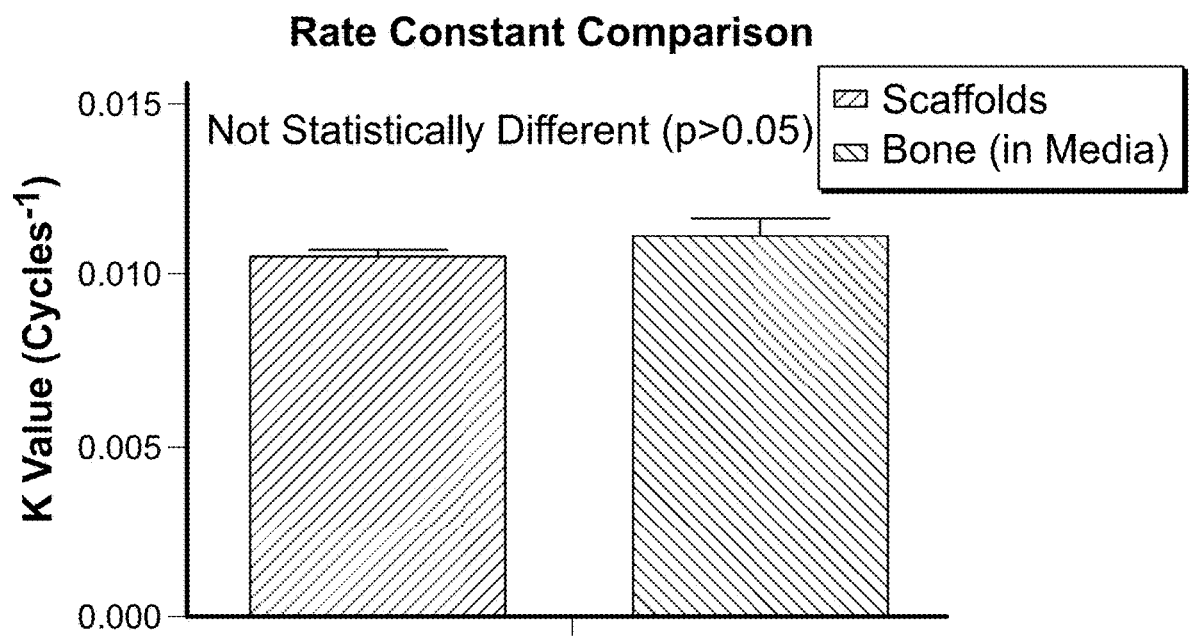
FIG. 23B is a graph of the K-Value, or rate constant, obtained from result of non-linear exponential regression of the scaffold shown in FIG. 22 and trabecular bone in media.

The deformation versus cycle number fatigue curve for both the trabecular bone specimens and 3D printed scaffolds displays a non-linear relationship and can be described by a one-phase decay exponential function, as shown in FIG. 23A. The slower, more gradual change versus the number of cycles applied is manifested by low value K parameters, which is favorable for cell seeding as it may lead to increased fluid flow due to internal pumping across the pores of the scaffold. In comparison to the K-values generated from the trabecular bone specimens subjected to axial compression, the K-values for the scaffolds were not statistically different ($p>0.05$) (see FIG. 23B). Such finding confirms the potential of the scaffold to encourage a biomechanically favorable environment.

Example 1D

Mechanical Testing: Indentation Analysis

Figure 24:
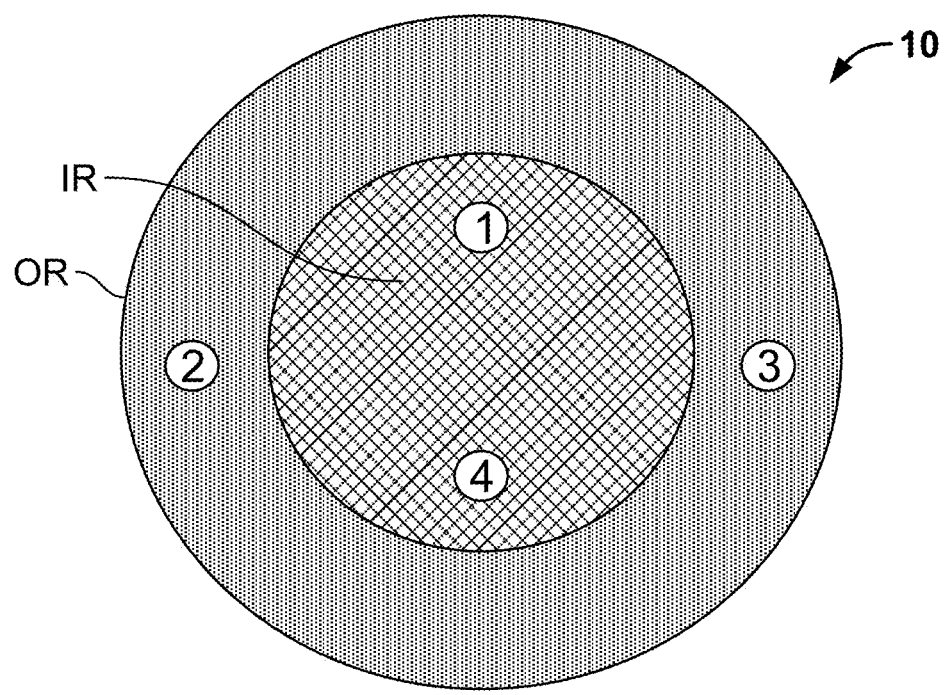
FIG. 24 is a schematic top view of a scaffold according to an embodiment of the present invention, with test sites identified on the surface of the scaffold for indentation testing, as discussed in Example 1D herein.

Six samples of the 3D printed scaffolds 10 were used to elucidate the region variations in mechanical properties. As illustrated in FIG. 24, four sites on each scaffold surface were identified (test sites 1 and 4 on the inside region IR, corresponding to the scaffold's inner core 16, and test sites 2 and 3 on the outside region OR, corresponding to the scaffold's outer core 18) and subjected to 1005 cycles of loading from −10N to −100N at a rate of 1 Hz using a 4 mm diameter indenter. Continuous load vs. deformation data was acquired beginning at cycle number 5 and at subsequent 50 cycle intervals thereafter. Deformation change at each cycle count was computed, averaged across each cycle count for each of the test sites 1-4, averaged between the respective inner and outer regions IR, OR of the scaffold surface, subjected to nonlinear analysis and to an F-test to determine whether single or dual exponential was the best fit (Prism 5.0, GraphPad Inc., San Diego, Calif.). Regression parameters produced K the rate constant, which is expressed in reciprocal of the X axis units (Cycles$_{−1}$) and is related to the rate at which the deformation value changes over the number of cycles. The regression parameters were examined using a 1-way ANOVA with a Tukey post hoc test for statistical comparison between the test site locations.

Figure 25A:
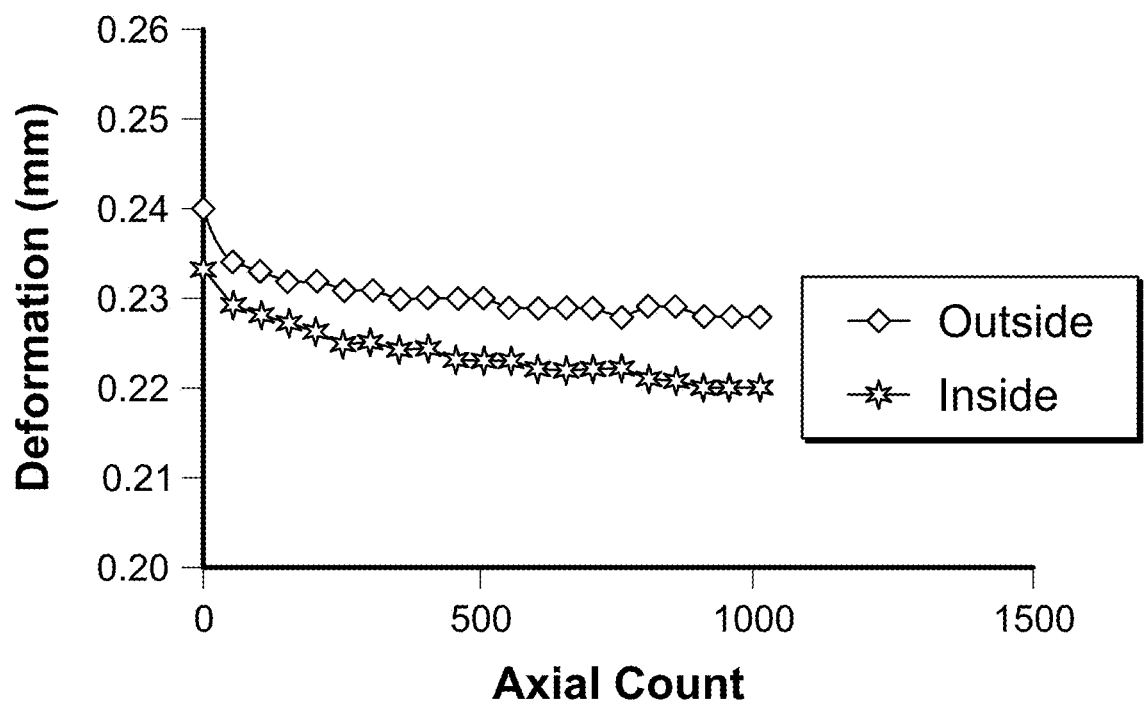
FIGS. 25A and 25B are graphs showing indentation test data, as discussed in Example 1D herein.
Figure 26:
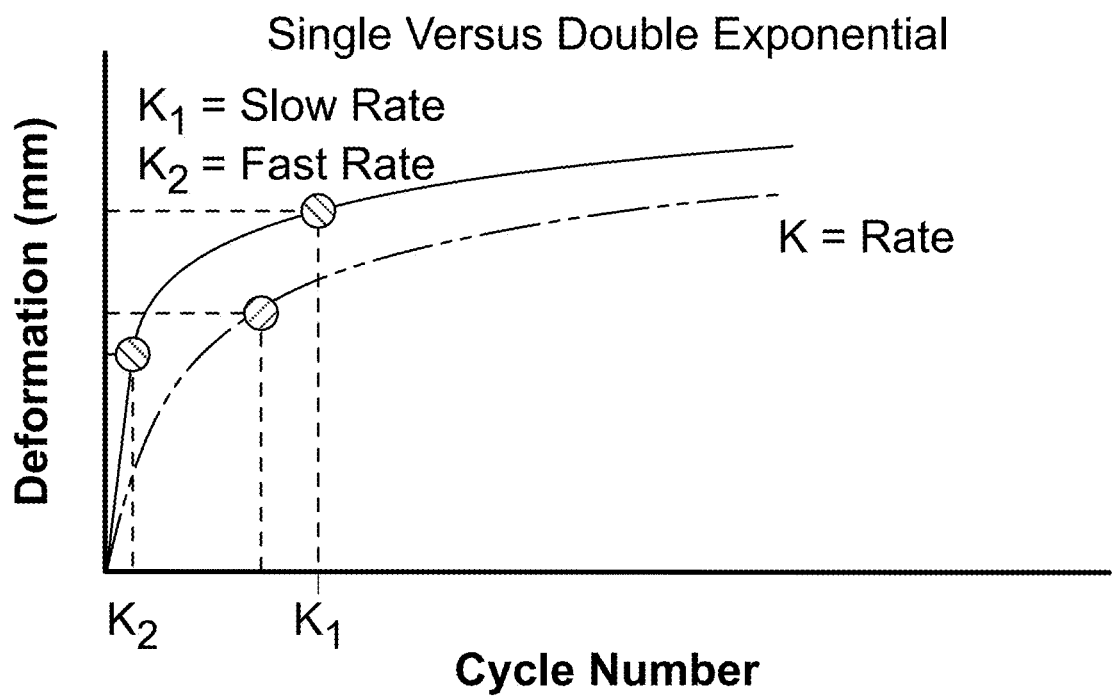
FIG. 26 is a graph showing single and double exponential regression in the indentation test data, as discussed in Example 1D herein.

The variance in test site location on the scaffold was examined by indentation testing, using a Bose ELF 3200 Materials Testing Machine. The deformation fatigue curve analysis resulted in dual exponential for all regions of the scaffold, as shown in FIG. 25A. The presence of a two-phase exponential can be interpreted as the presence of a solid and a fluid component in the structure, thereby producing a slow and fast component from the nonlinear regression analysis. The solid component attributes to maintaining a stable mechanical framework and the fluid component attributes to allowing fluid flow of nutrient and oxygen exchange. The graph of FIG. 26 shows a representation of slow and fast components of K, the rate constant in a single versus dual exponential function.

Figure 25B:
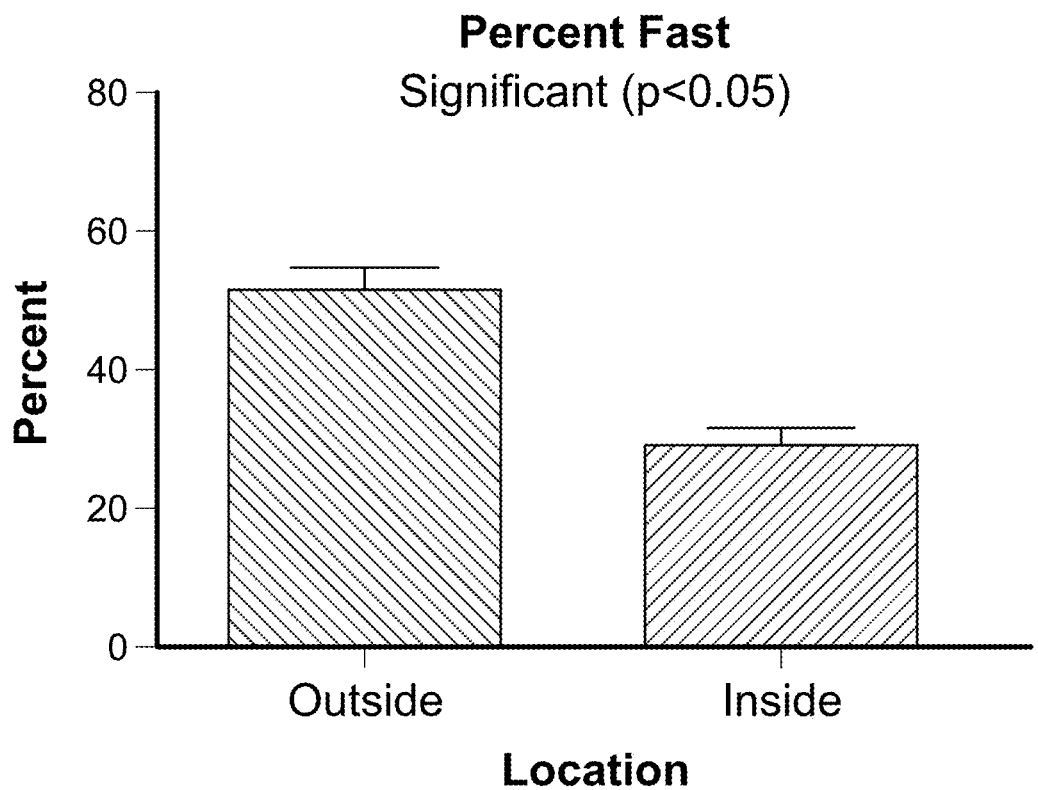

The deformation fatigue curve analysis resulted in dual exponential for all regions of the scaffold. The slower and gradual deformation changes versus the number of cycles applied based on the low value K parameters may be indicative of gradual mechanical changes due to increased fluid flow while the more rapid K values can be representative of the solid phase within the scaffold (see FIG. 25A). Percent Fast is calculated based on the ratio between the $K_{fast}$ and $K_{slow}$. The outer region OR possessed a greater percent of $K_{fast}$ compared to the inner region IR, which is expected as the outer region contributes to maintaining the structural integrity of the scaffold (see FIG. 25B). Further, such behavior is favorable for cell seeding as it leads to increased permeation of nutrient fluid flow toward the inner regions of the scaffold under cyclic loading. This confirms that scaffold mechanical properties can be optimized to permit biological transmission between regions of the scaffold while mimicking native bone tissue.

Example 1E

Mechanical Testing: Fatigue Endurance Analysis

Figure 27:
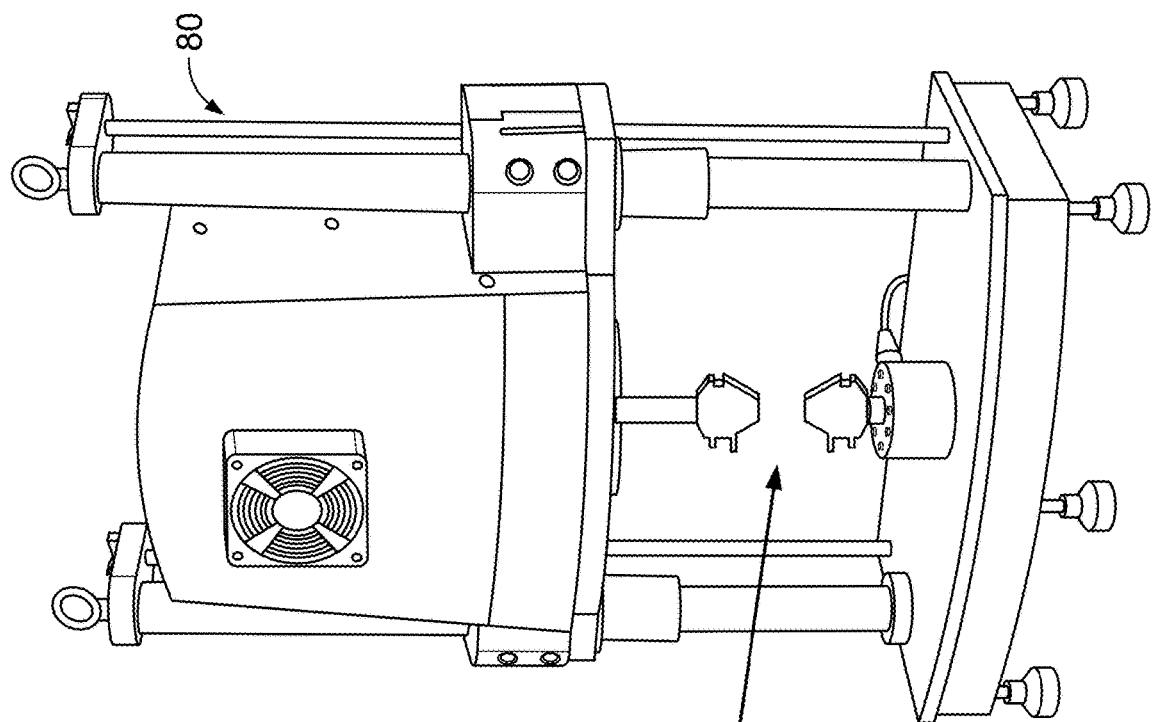
FIG. 27 is a schematic view of an experimental test set up for fatigue endurance mechanical analysis of a scaffold according to an embodiment of the present invention, as discussed in Example 1E herein.
Figure 27:
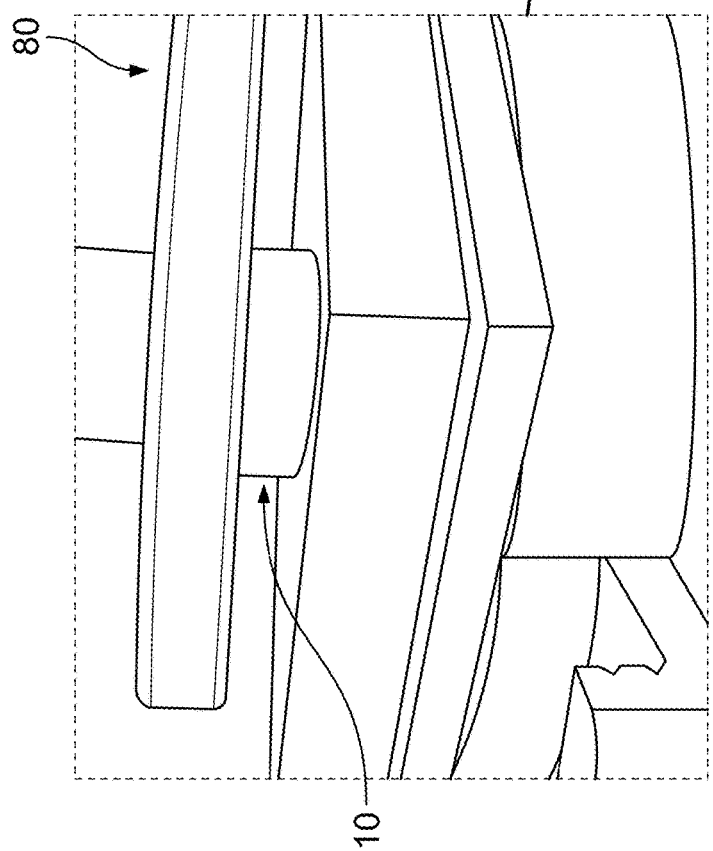

To determine its fatigue mechanical properties, we tested the scaffold 10 (N=8) under cyclic deformation using a materials testing machine 80 (Bose ELF3300, Eden Prairie, Minn.) (see FIG. 27). Similar to the ASTM F2077 Standard, pairs of scaffolds 10 were subjected to compressive sinusoidal fatigue loading at each of the following loads for 5 million cycles: 800N, 1000N, 1400N, and 1800N. All fatigue loading was performed with an R value of 10. Continuous load vs. deformation data was acquired beginning at cycle number 500 and at subsequent 250,000 cycle intervals thereafter. Deformation change at each cycle count was computed, averaged across each cycle count, and subjected to nonlinear analysis (Prism 5.0, GraphPad Inc., San Diego, Calif.). The parameters produced from the nonlinear exponential regression were analyzed as previously described. Half-life (ln(2)/K), which represents the number of cycles required to achieve 50% reduction in $Y_0$, was also computed. The change in % strain and deformation over the course of the fatigue test was also computed.

Figure 28A:
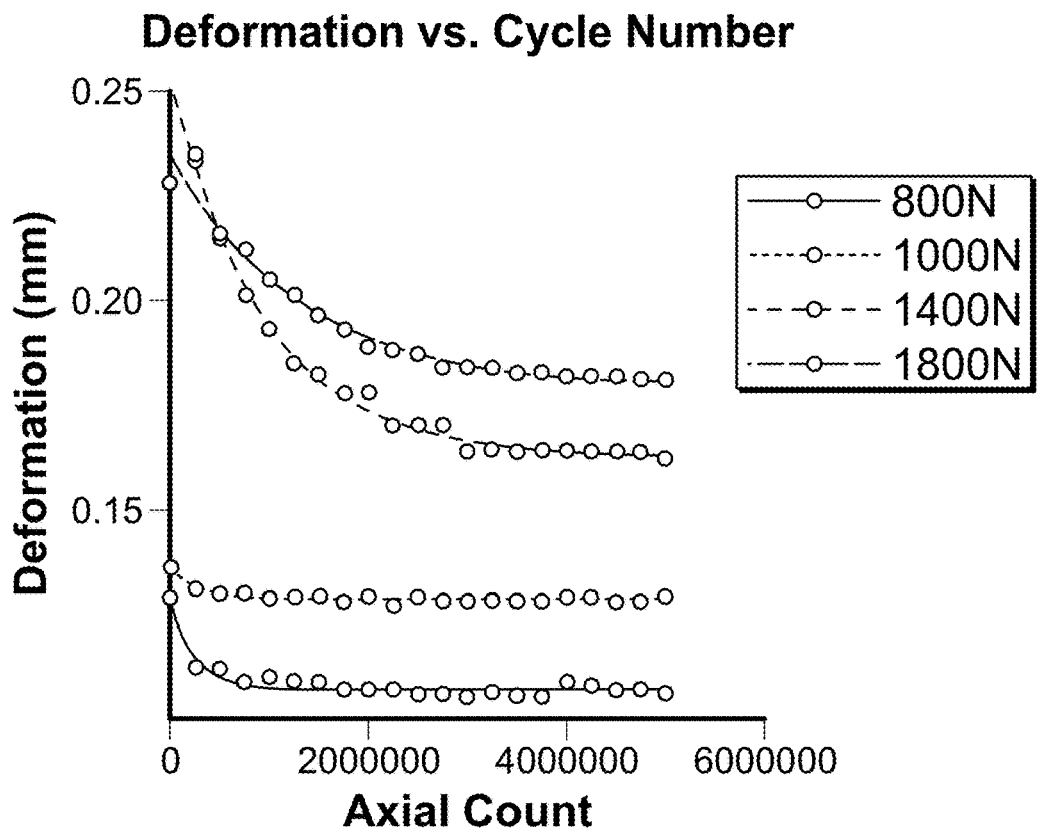
FIG. 28A is a graph showing change in deformation over the course of the fatigue test, based on the fatigue endurance mechanical analysis data, as discussed in Example 1E herein.
Figure 28B:
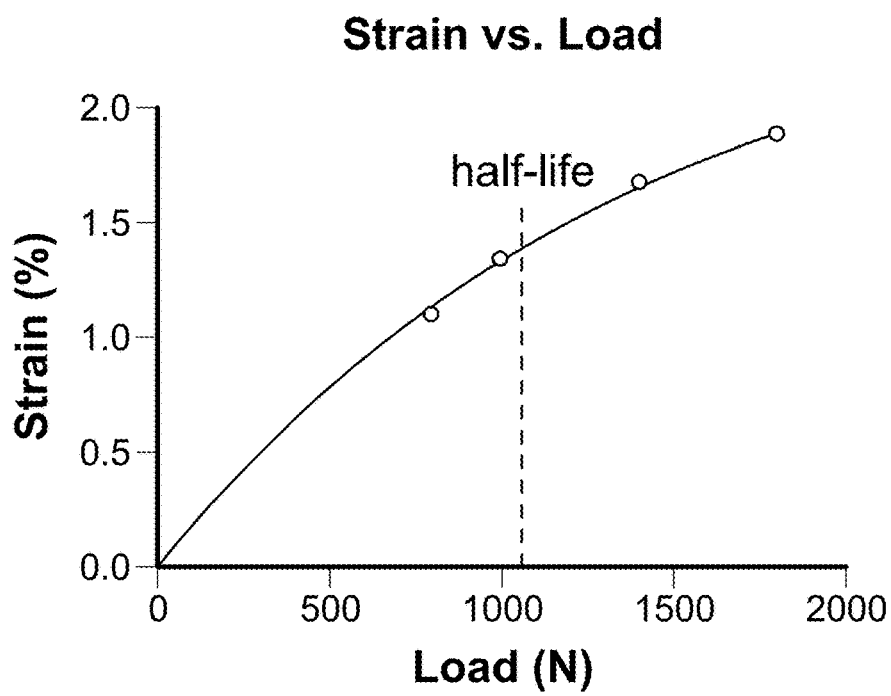
FIG. 28B is a graph showing non-linear exponential fit of the percent strain versus load curve, based on the fatigue endurance mechanical analysis data, as discussed in Example 1E herein.

The results of the cyclic fatigue test produced a single exponential decay of decreasing deformation versus cycle number, as shown in FIG. 28A. The strain at the final deformation at each load level was computed and the Percent Strain versus Load expressed a nonlinear relationship, as shown in FIG. 28B. The half-life was calculated based on the relationship half-life=ln(2)/K, and determined to be approximately 1017±11 N. This indicates that at 1.3 times greater than the adult body weight, the scaffold of the present invention is capable of maintaining the required mechanical strength to support the body. This may be attributed to the horizontal conduits in the scaffold (see FIGS. 17 and 18A), which not only enable fluid flow throughout but also serve to distribute compressive load evenly. The strain half-life was determined to be 1.4%, which is ideal since bone can withstand maximum strain values of approximately 2% (see FIG. 28B). Technically, all four load levels passed as their strain levels were below 2%. Further, at 800N which is twice the torso weight, the scaffold is able to reach stability at approximately 200,000 cycles, which correlates to 10 weeks post-surgery (see FIG. 28A) Thus, use of this scaffold exhibits potential to minimize the need for internal or external fixation systems that are typically used in conjunction with segmental bone repair surgeries to provide stability and support.

Example 1F

Cell Seeding on Scaffold

Figure 29:
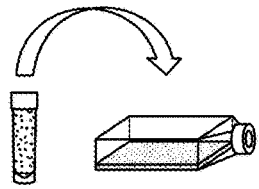
FIG. 29 is a schematic view of the process for examining cytocapability of the scaffold constructed in accordance with the present invention, as discussed in Example 1F herein.
Figure 29:
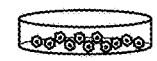

Cell attachment and penetration throughout all regions of the scaffold were examined after cell seeding to confirm that the scaffold provided a biologically favorable environment for bone growth. With reference to FIG. 29, Human Fetal Osteoblasts (hFOB 1.19) (ATCC, Manassas, Va.) were cultured in a T-75 flask and a humidified incubator buffered with 5% CO2 until it reached confluency. The scaffold was sterilized by immersing in 70.0% isopropyl alcohol for two hours, followed by two hours of UV light. Then, the scaffold was washed three times with Dulbecco's Modified Phosphate Buffered Saline (ThermoFisher Scientific, Waltham, Mass.) and then three times with culture media (Dulbecco's Modified Eagle Medium supplemented with 10% fetal bovine serum and 1% stryptomyocin (ThermoFisher Scientific, Waltham, Mass.). Once confluency was reached, the hFOBs were detached from the walls of the flask and seeded onto the scaffold at a concentration of $8.0 \times 10^5$ cells/mL. The seeded scaffold was left to sit for two hours on an orbital shaker to maximize media flow throughout and then replenished with 6.0 mL of culture media. The cell-seeded scaffold was cultured for a week in an incubator at 37° C. and 5% $CO_2$ while changing media every other day. On the last day, the cells in the seeded scaffold were fixed using 4% paraformaldehyde stained with 0.05% methylene blue for microscopic imaging analysis using a VHX-5000 Digital Microscope (Keyence, Itaska, Ill.).

Figure 30A:
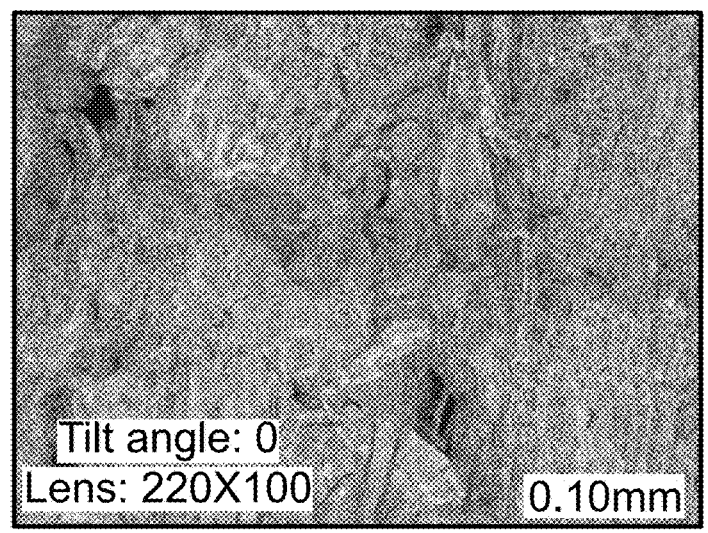
FIG. 30A is a photograph of a stereoscopic view of the outer core of the scaffold according to an embodiment of the present invention, as seeded with cells and stained with methylene blue, captured at 100× magnification, as discussed in Example 1F herein.
Figure 30B:
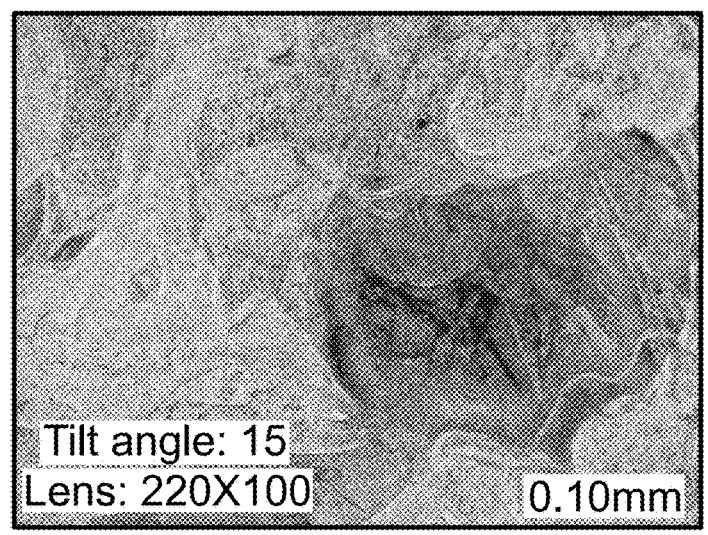
FIG. 30B is a photograph of a stereoscopic view of the inner core of the scaffold according to an embodiment of the present invention, as seeded with cells and stained with methylene blue, captured at 100× magnification, as discussed in Example 1F herein.

Based on the methylene blue staining of the scaffold seeded with human fetal osteoblasts in a 1-week culture, observations under microscopic imaging revealed that the seeded cells penetrated through all regions of the scaffold, as indicated by dark dots that are nuclei stained by the methylene blue (see FIGS. 30A and 30B). This validated the ability for nutrient exchange to be sustained throughout the scaffold, and confirmed its cytocompatible capabilities to yield a biologically favorable environment for bone growth.

Example 1G

Effects of Mechanical Stimulation on Cell Seeded Scaffolds

While the scaffold was successfully seeded as previously described in Example 1F and confirmed by methylene blue staining, bone growth is a dynamic process where continued remodeling is essential for the maintenance of bone health. It is well recognized that bone will remodel in accordance to the mechanical environment, as stated by Wolff's Law. Studies have noted that bone tissues respond to strains of 0.1% to 0.35% from everyday activities and above this range triggers bone formation and below it results in bone resorption. Thus, the effects of mechanical loading of cell-seeded scaffolds were examined under in vitro conditions, with the expectation that a specific loading frequency will induce an optimal bone response.

The exact nature of loading conditions experienced by cells within bone structures that influence the response of mechanical loading remains unclear. To date, much of the focus has been on in vivo models, with few on in vitro conditions. In 2015, Tanaka et al. studied the mechanically stimulated osteogenic response of osteoblast seeded scaffolds subjected to a wide range of frequencies from 0.2 Hz to 60 Hz. Results revealed that mechanical stimulation at 2 Hz showed the greatest proliferative and mineralization response in vitro among all of the loading frequencies examined.

Figure 31:
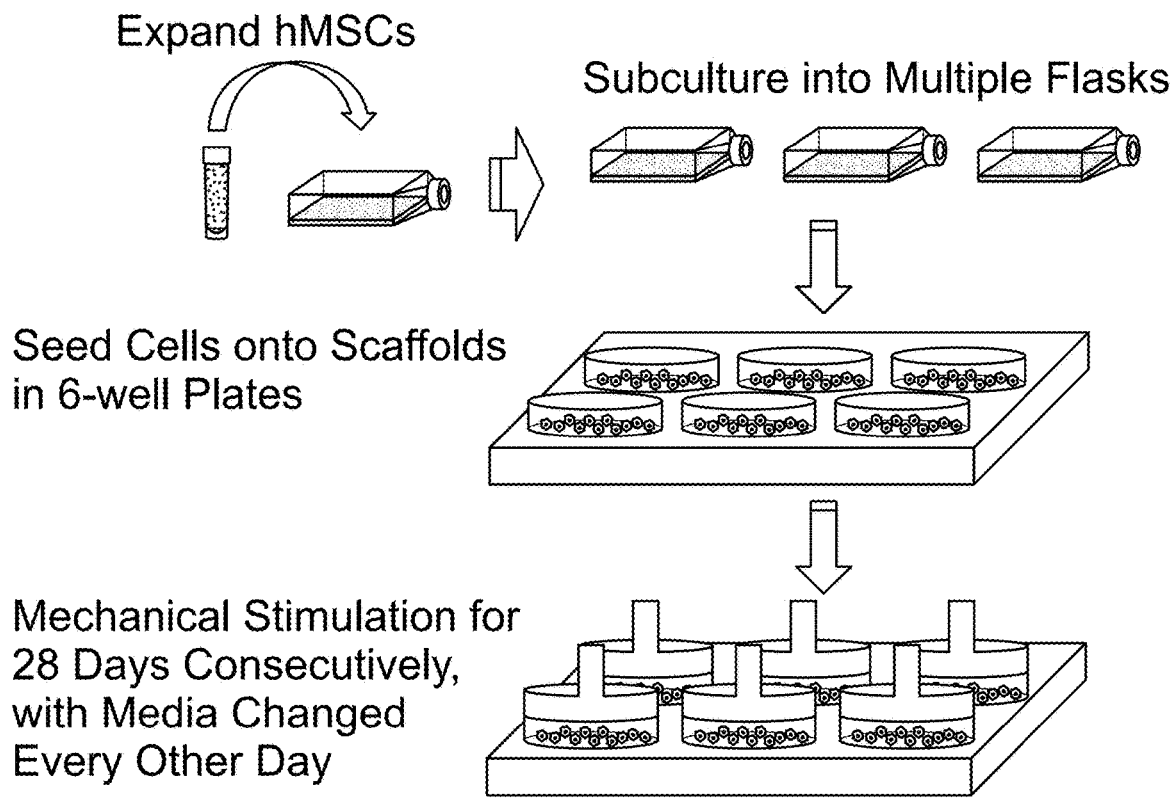
FIG. 31 is a schematic view of the process for achieving cell-seeded scaffolds according to an embodiment of the present invention, with daily mechanical stimulation, as discussed in Example 1G herein.

Modeled after Tanaka et al., the scaffolds were subjected to a broad range of frequencies (i.e., 0.5 Hz, 2 Hz, 5 Hz), and a set of scaffolds with no stimulation were used as the control. Six scaffolds were tested for each group. As illustrated in FIG. 31, human mesenchymal stem cells (hMSCs) (PromoCell, Heidelberg, Germany) were cultured in T-150 flasks and grown to confluency. In parallel, each group of scaffolds was sterilized by immersing in 70.0% isopropyl alcohol for two hours. Then, each scaffold was washed three times with Dulbecco's Modified Phosphate Buffered Saline (ThermoFisher Scientific) and then three times with Mesenchymal Stem Cell Growth Media (PromoCell, Heidelberg, Germany), supplemented with its serum and 1% stryptomyocin (ThermoFisher Scientific, Waltham, Mass.). Confluent hMSCs were detached from the walls of the flask and seeded onto each scaffold at a concentration of $8.0 \times 10^5$ cells/mL. The seeded scaffolds were left to sit for two hours on an orbital shaker to maximize media flow throughout and then replenished with 6.0 mL of culture media. On the following day, the scaffolds were transferred to new wellplates and media was changed. The cell-seeded scaffolds were cultured in an incubator at 37° C. and 5% $CO_2$ while changing media every other day. The hMSCs were differentiated to osteoblasts using Osteogenic Differentiation Media, according to the manufacturer's protocol. (PromoCell, Heidelberg, Germany) The scaffolds were subjected to daily mechanical stimulation for 28 consecutive days.

Osteoblast lineage cells possess a two phase growth and differentiation phase with three distinct stages; proliferation, extracellular matrix maturation, and mineralization. Proliferation occurs more rapidly during the first two weeks, and is marked by the induction of collagenous extracellular matrix, with extracellular matrix mineralization observed by the third and fourth week. Therefore, it was critical that the mechanical stimulation of the cell-seeded scaffolds were carried out for a minimum of 28 days.

Figure 32:
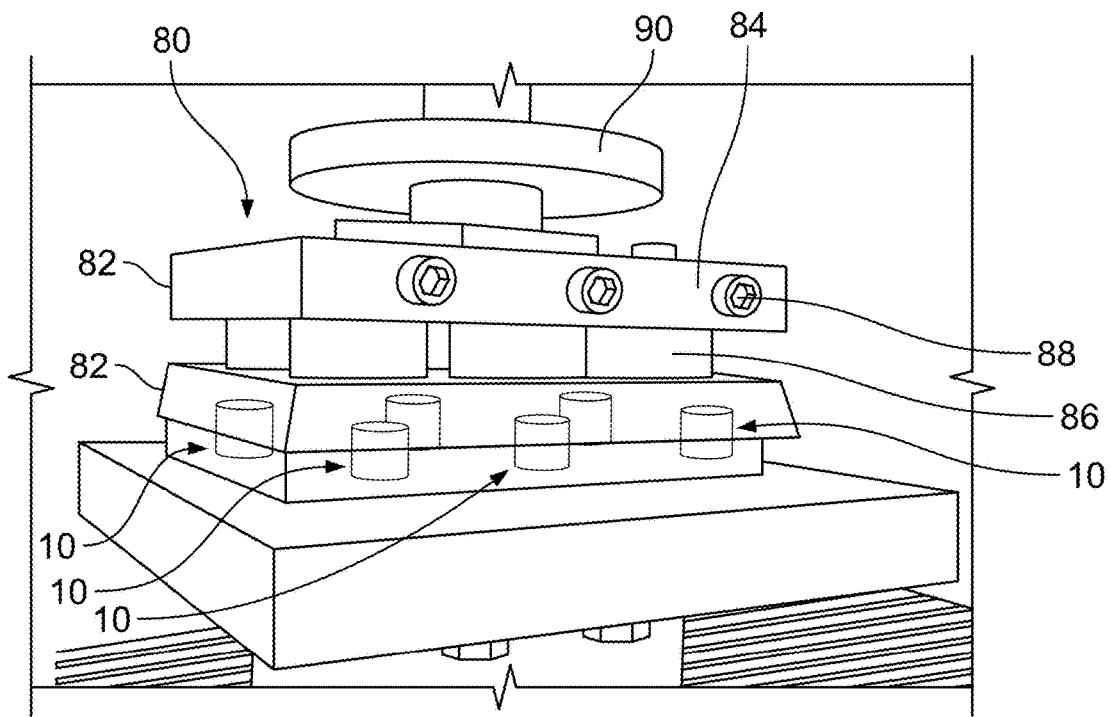
FIG. 32 is a top perspective view of the experimental setup for mechanical stimulation of cell-seeded scaffolds according to an embodiment of the present invention, as discussed in Example 1G herein.
Figure 33A:
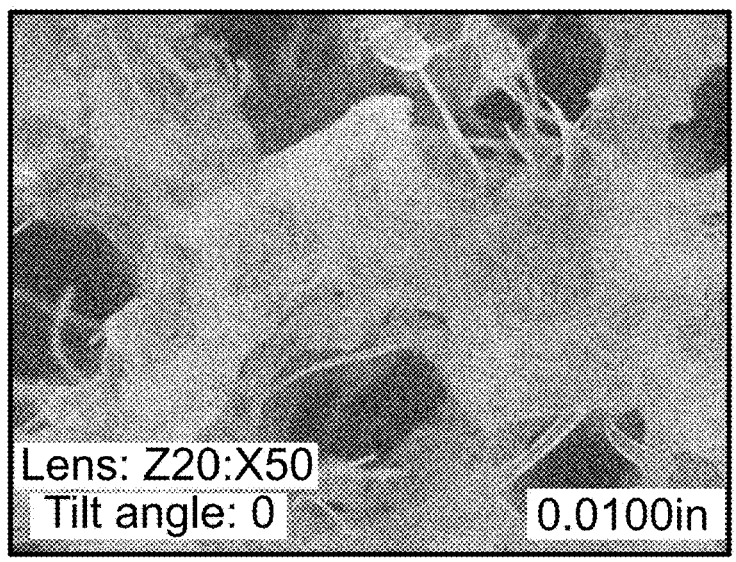
FIGS. 33A and 33B show the results of Alizarin Red staining of the control group of scaffolds according to an embodiment of the present invention that did not undergo daily mechanical stimulation (scaffold outer core shown in A and scaffold inner core in B), as discussed in Example 1G herein.
Figure 33B:
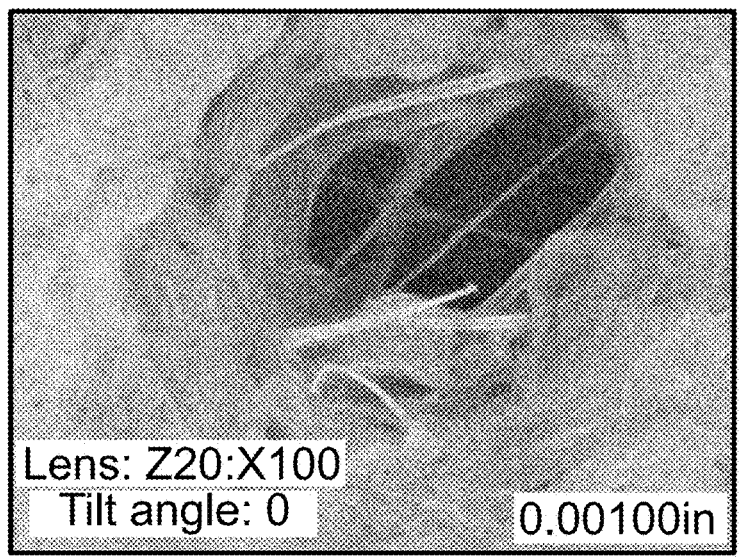
Figure 34A:
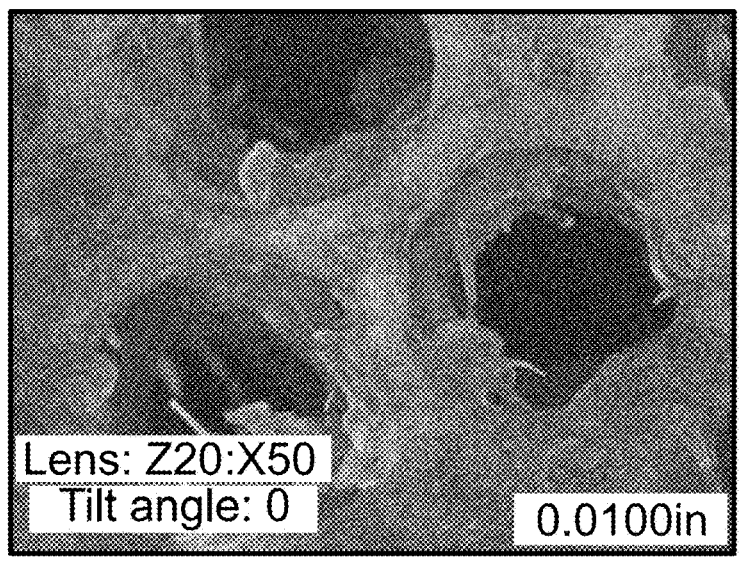
FIGS. 34A and 34B show the results of Alizarin Red staining of the group of scaffolds according to an embodiment of the present invention that were subjected to daily mechanical stimulation of 2 Hz (scaffold outer core shown in A and scaffold inner core in B), as discussed in Example 1G herein.
Figure 34B:
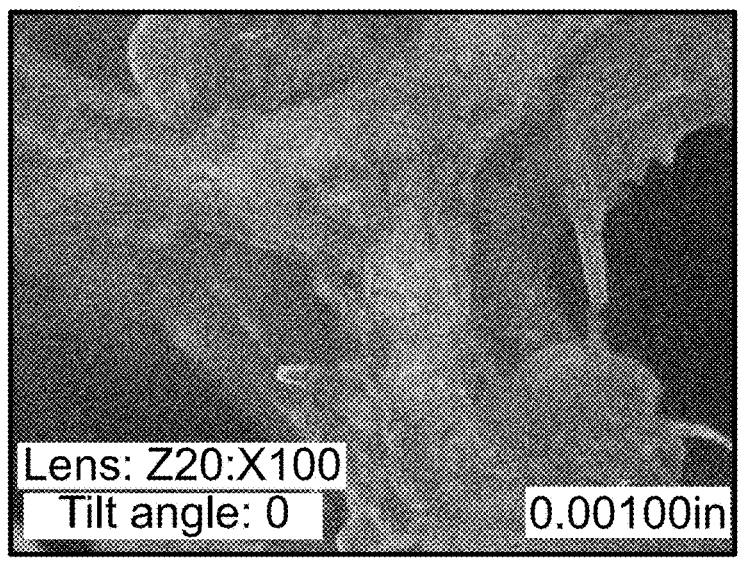
Figure 35A:
FIGS. 35A and 35B show the results of Alizarin Red staining of the group of scaffolds according to an embodiment of the present invention that were subjected to daily mechanical stimulation of 0.5 Hz (scaffold outer core shown in A and scaffold inner core in B), as discussed in Example 1G herein.
Figure 35B:
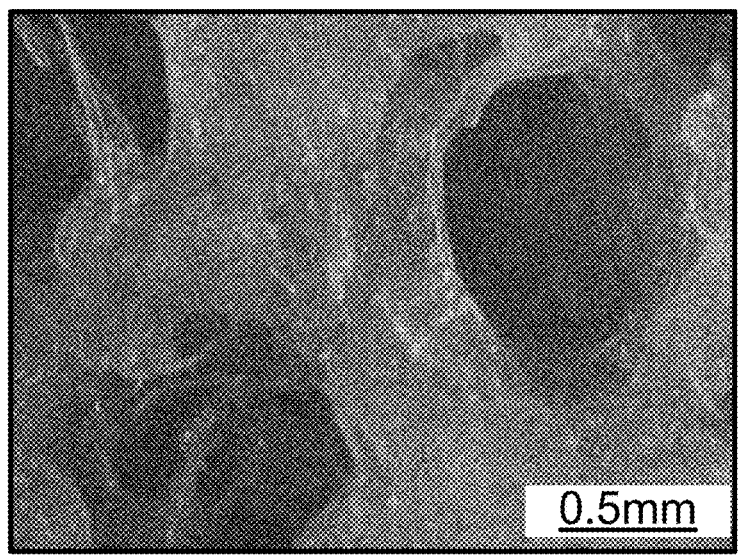
Figure 36A:
FIGS. 36A and 36B show the results of Alizarin Red staining of the group of scaffolds according to an embodiment of the present invention that were subjected to daily mechanical stimulation of 5 Hz (scaffold outer core shown in A and scaffold inner core in B), as discussed in Example 1G herein.
Figure 36B:
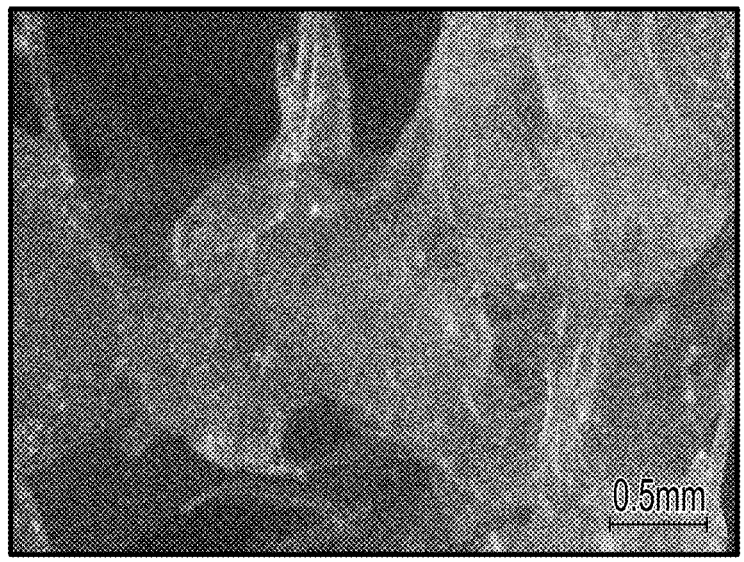
Figure 37A:
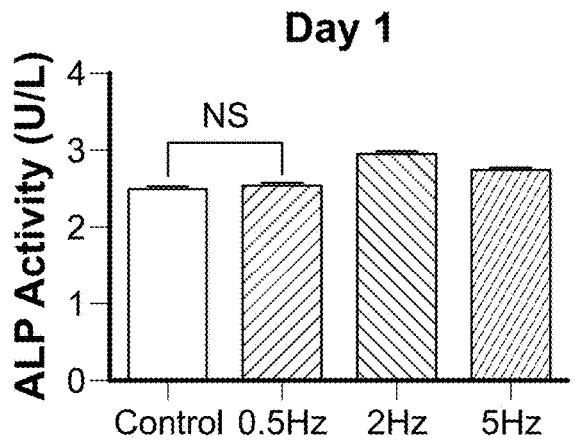
FIGS. 37A-E show the results of 1-ANOVA repeated measures test with Tukey post hoc test to statistically compare differences in time points from the results of the alkaline phosphatase activity assay on the scaffolds according to an embodiment of the present invention, as discussed in Example 1G herein.
Figure 37B:
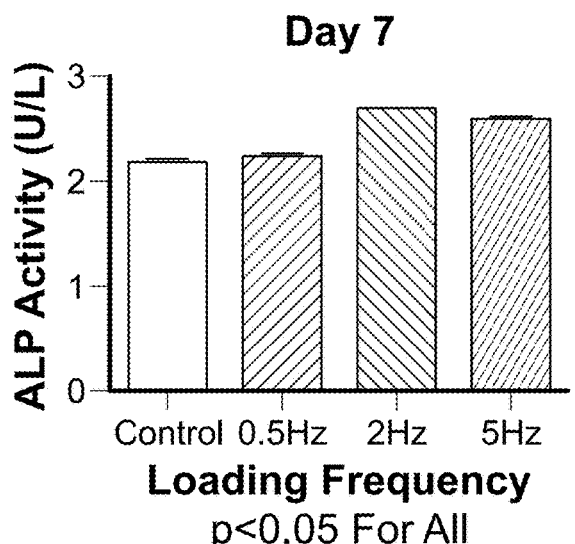
Figure 37C:
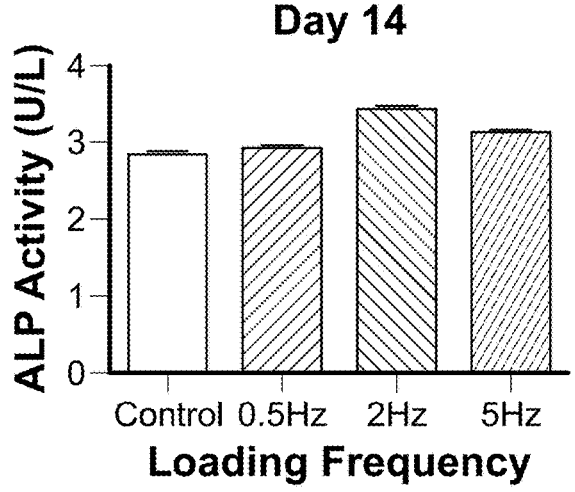
Figure 37D:
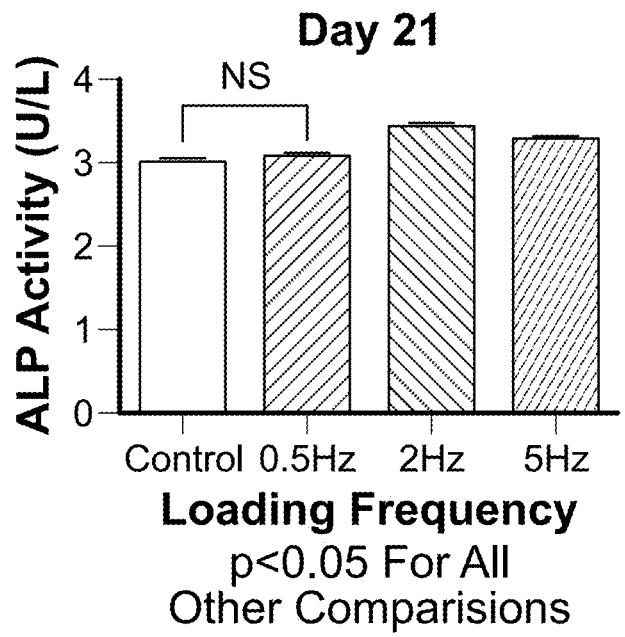
Figure 37E:
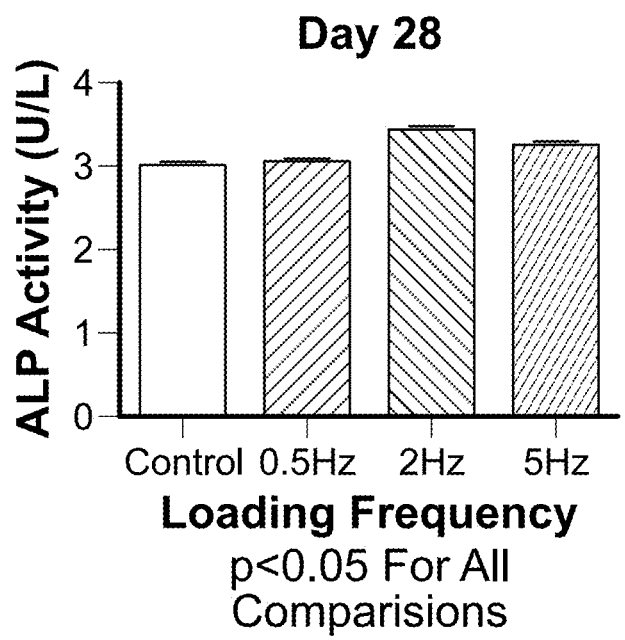
Figure 38A:
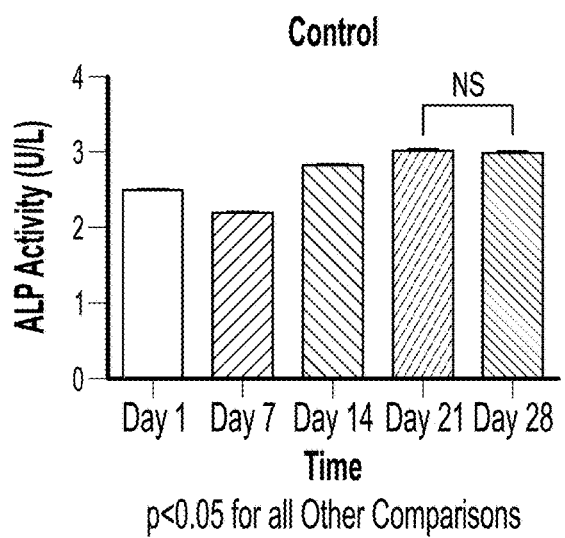
FIGS. 38A-D show the results of 1-ANOVA repeated measures testing with Tukey post hoc testing to statistically compare differences in loading frequency groups from results of the alkaline phosphatase activity assay on the scaffolds according to an embodiment of the present invention, as discussed in Example 1G herein.
Figure 38B:
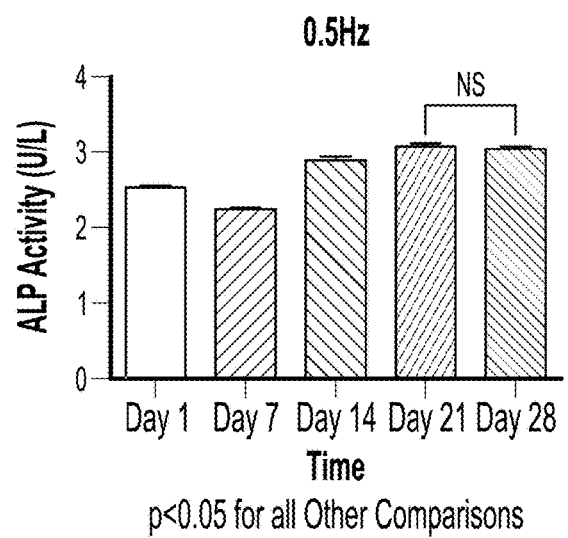
Figure 38C:
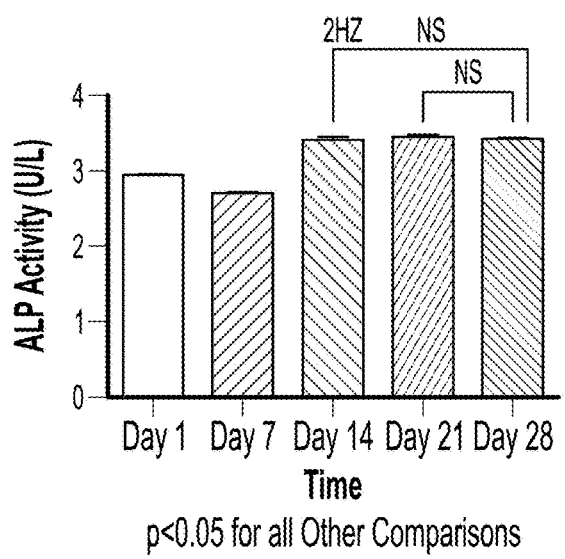
Figure 38D:
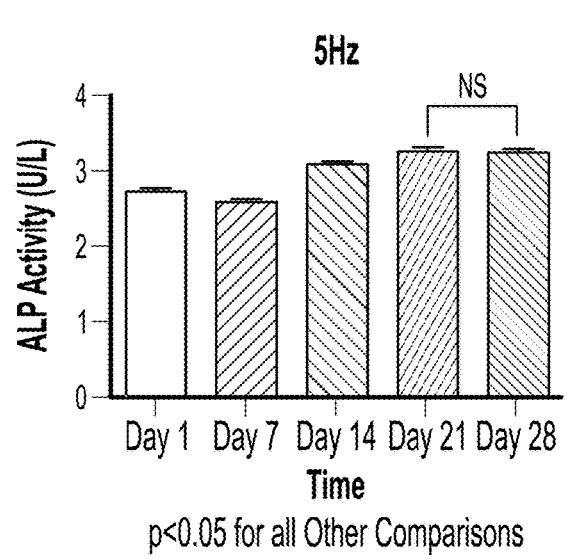
Figure 39A:
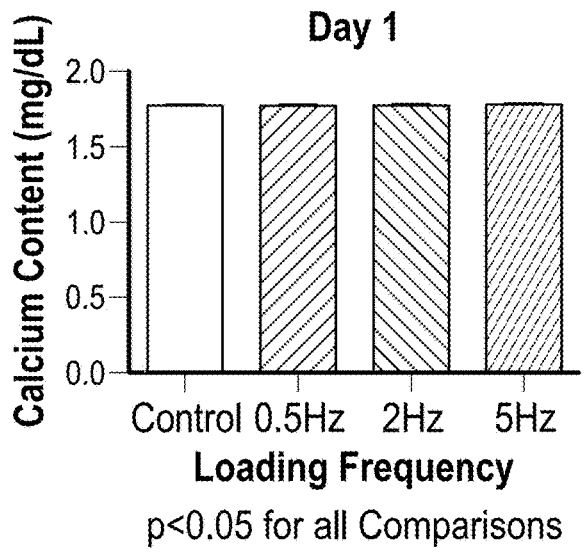
FIGS. 39A-E show the results of 1-ANOVA repeated measures testing with Tukey post hoc testing to statistically compare differences in time points from results of the calcium colorimetric assay on the scaffolds according to an embodiment of the present invention, as discussed in Example 1G herein.
Figure 39B:
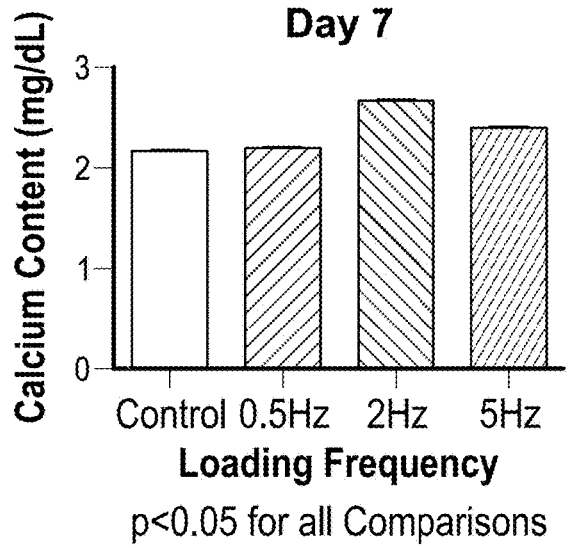
Figure 39C:
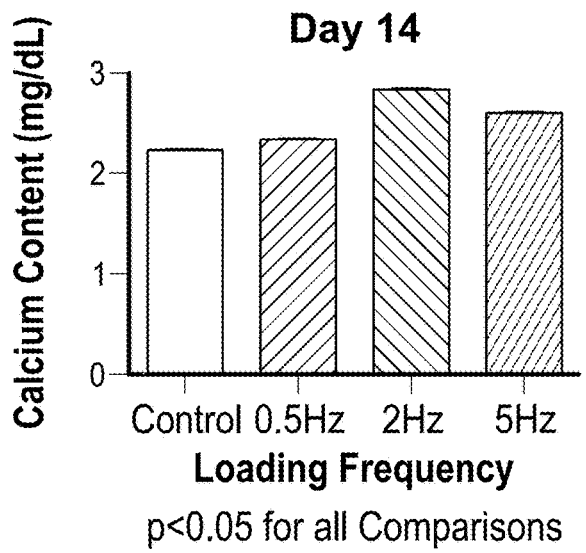
Figure 39D:
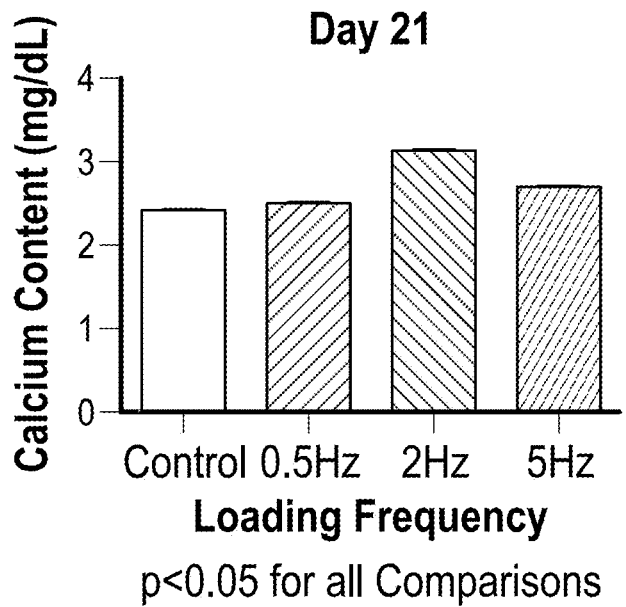
Figure 39E:
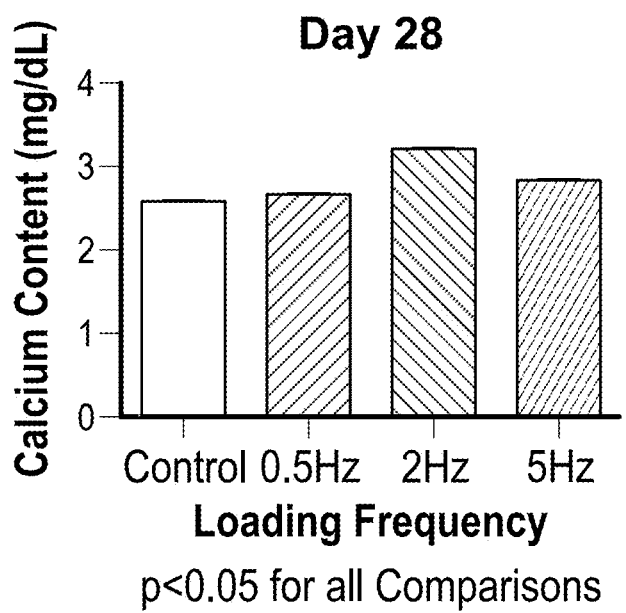
Figure 40A:
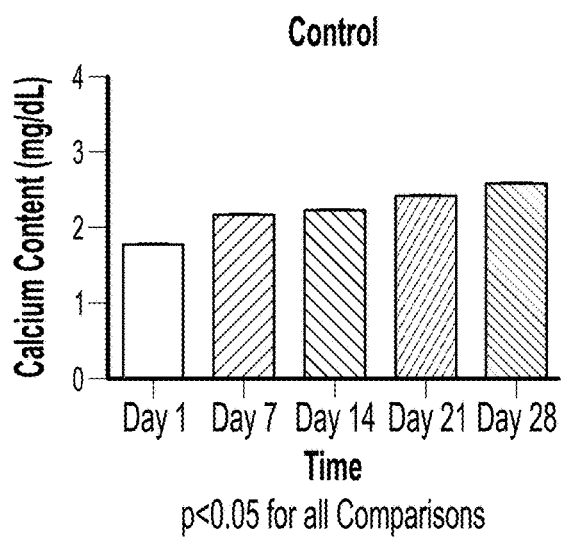
FIGS. 40A-D show the results of 1-ANOVA repeated measures testing with Tukey post hoc testing to statistically compare differences in loading frequency from results of the calcium colorimetric assay on the scaffolds according to an embodiment of the present invention, as discussed in Example 1G herein.
Figure 40B:
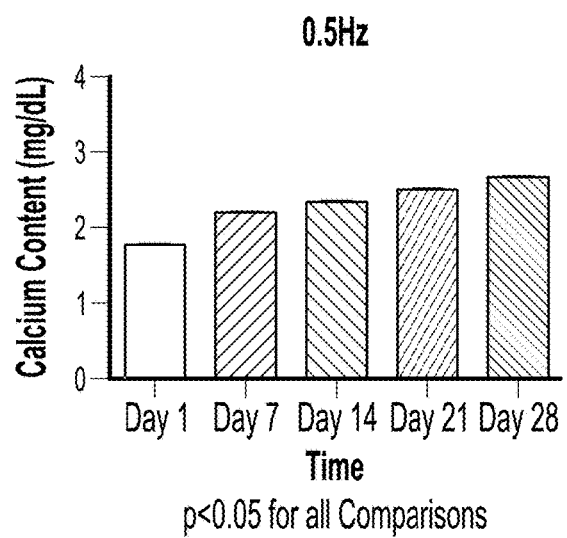
Figure 40C:
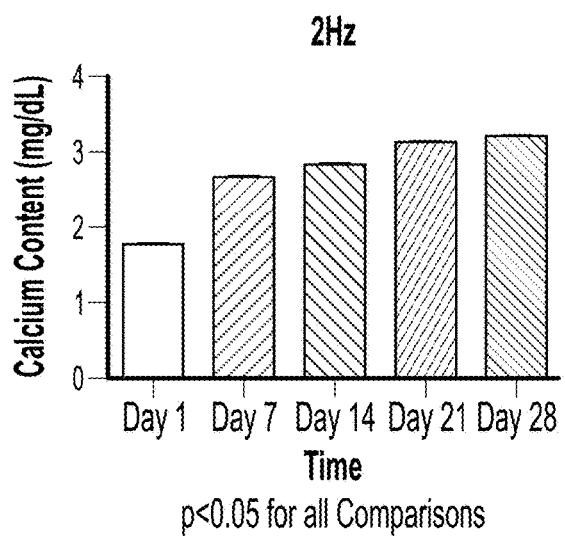
Figure 40D:
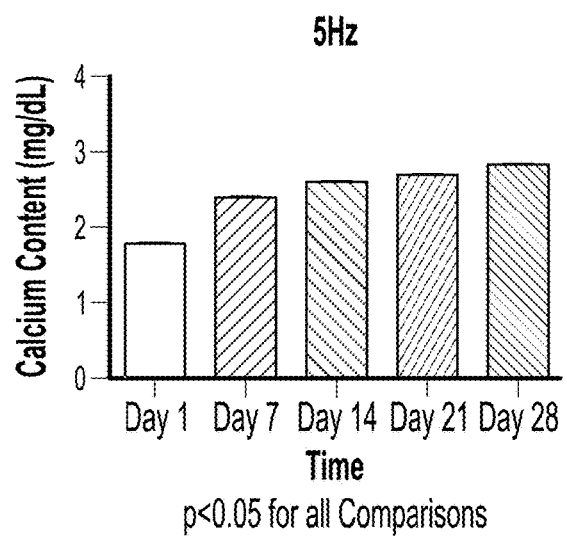

Each group of scaffolds was subjected to mechanical stimulation using a Bose ELF 3300 materials testing machine 80 (see FIG. 32). In order to maintain a sterile environment for the seeded scaffolds 10, a thin film membrane sheet that permeated $O_2/CO_2$ gas exchange sealed the 6-well plate prior to removal from the cell culture hood and placed onto the mechanical testing machine (Breathe EZ Film Sheet, USA Scientific). A custom designed 3D printed test fixture 82 was aligned with the 6-well plate of scaffolds 10, as illustrated in FIG. 32.

It has been reported that under in vitro conditions, bone cells require 1-10% strain to respond to mechanical stimulation. However, Turner et al. noted that prolonged stimulation cause bone cells to reach a saturated state at which they experience mechanosensory desensitization. Further, incorporation of a 24 hour rest period enables 98% of mechanosensitivity to be restored. Therefore, sinusoidal compressive loading was applied to the scaffolds at 2.5% strain for 360 cycles at a rate of 2 Hz daily for 28 consecutive days with a 24 hour rest period between stimulations. This procedure was repeated for the other groups at 0.5 Hz and 5 Hz respectively, as set out in Table 2.

TABLE 2

Loading regimen for the four scaffolds groups

| Loading Frequency | Load per scaffold | Cycles per day | # of Scaffolds |
| --- | --- | --- | --- |
| Control (no mechanical stimulation) | 35N | 360 | 6 |
| 2 Hz | 35N | 360 | 6 |
| 0.5 Hz | 35N | 360 | 6 |
| 5 Hz | 35N | 360 | 6 |

With further reference to FIG. 32, the custom-designed test fixture 82 was 3D printed to allow for multiple scaffolds 10 to be cyclically loaded at once. Designed in accordance to the geometries of a 6-well plate, the test fixture 82 includes a rectangular base 84 with six plungers 86 and M-6 screws 88 to lock the plungers 86 into the base 84. Uniform stress/strain on each scaffold 10 was achieved by the mass of each associated plunger 86 residing upon the entire scaffold surface to permit a uniform preload to each scaffold 10. The screws 88 fasten in place the plungers 86, and the loading test fixture 82 is then secured to the actuator 90 of the testing machine 80. The test fixture 82 enables controlled deformation and equivalent loading to all scaffold samples.

Proliferating cells show alkaline phosphatase (ALP) activity, which increases during in vitro bone formation. Thus, the alkaline phosphatase activity was monitored regularly every other day when media was changed using an ALP Assay Kit (Abcam, Boston, Mass.) and followed according to manufacturer's protocol. While the alkaline phosphatase assay kit is useful in monitoring the functional activity of the cell seeded scaffolds, alkaline phosphatase is not limited to osteoblasts. Thus, additional confirmation such as quantifying the calcium deposits for mineralization is necessary. The calcium deposition was quantified on a weekly basis using a calcium colorimetric assay kit, according to the manufacturer's protocol (BioVision, San Francisco, Calif.).

Calcium deposits are an indication of successful in vitro bone formation and can be stained using Alizarin Red staining. After the scaffold groups (0.5 Hz, 2 Hz, and 5 Hz) were subjected to 28-day mechanical stimulation, all of the scaffolds, including the control group were fixed and stained using Alizarin Red staining to compare the mineralization across all of the groups, as shown in FIGS. 33A-36B. These microscopic images were taken using a VHX-5000 Digital Microscope (Keyence, Itasca, Ill.).

Based on the result of the Alizarin Red staining which stained the calcium deposits in the scaffold, it was evident that there was more calcification in the mechanically stimulated scaffolds compared to the scaffolds that were not subjected to daily loading. The scaffolds mechanically stimulated at 2 Hz showed the highest mineralization, followed by 5 Hz, 0.5 Hz, and then the control (see FIGS. 33A-36B).

The results from the alkaline phosphatase activity and calcium colorimetric assays were both statistically analyzed via repeated measures 1-way ANOVA tests. One analysis was used to examine differences in loading frequency, and the other was used to examine differences in time points throughout the course of the 28-day mechanical stimulation experiment. Both analyses employed a Tukey's post hoc test for comparison between the respective groups.

For alkaline phosphatase activity, the 1-way ANOVA statistical analyses for comparison of time points (as shown in FIGS. 37A-E) similarly revealed that the means were statistically significant ($p<0.001$) and comparison of all loading frequencies were statistically significant ($p<0.05$), with the exception of no significant difference observed between the control and 0.5 Hz group on Day 1 and Day 21. This suggests that perhaps 0.5 Hz loading frequency did not trigger as much of a stimulatory effect on the proliferative response of bone.

For the 1-way ANOVA statistical analyses for comparison of loading frequencies revealed that the means were statistically significant ($p<0.001$), as shown in FIGS. 38A-D. For all loading frequency groups, aside from Day 21 and Day 28, comparison of all other time points were statistically significant ($p<0.05$). This is indicative that the cell proliferative response reached its maximum by Day 21. Further, there was no statistical significance observed at Day 14 for the 2 Hz group, which is indicative that it proliferated faster compared to the other loading frequency groups, maxing out by Day 14 during the 28-day dynamic culture.

Regarding the data collected from Calcium Colorimetric assays to quantify calcium content, the 1-way ANOVA statistical analyses for comparison of time points revealed that the means were statistically significant ($p<0.001$), as shown in FIGS. 39A-E. Further, all comparisons between the groups in the Tukey post hoc tests revealed that all comparisons were also statistically significant (p<0.05). The 2 Hz group was statistically higher compared to the rest of the loading frequency groups, which confirms that it mineralized more and at a faster rate.

Regarding the data collected from Calcium Colorimetric assays to quantify calcium content, the 1-way ANOVA statistical analysis for comparison of loading frequency revealed that the means were statistically significant (p<0.001), as shown in FIGS. 40A-D. Further, all comparisons between the groups in the Tukey post hoc tests revealed that all comparisons were also statistically significant (p<0.05). All groups displayed a statistically increased trend from Day 1 to Day 28.

Example 1H

Post-Mechanical Stimulation Fatigue Analysis

Figure 41:
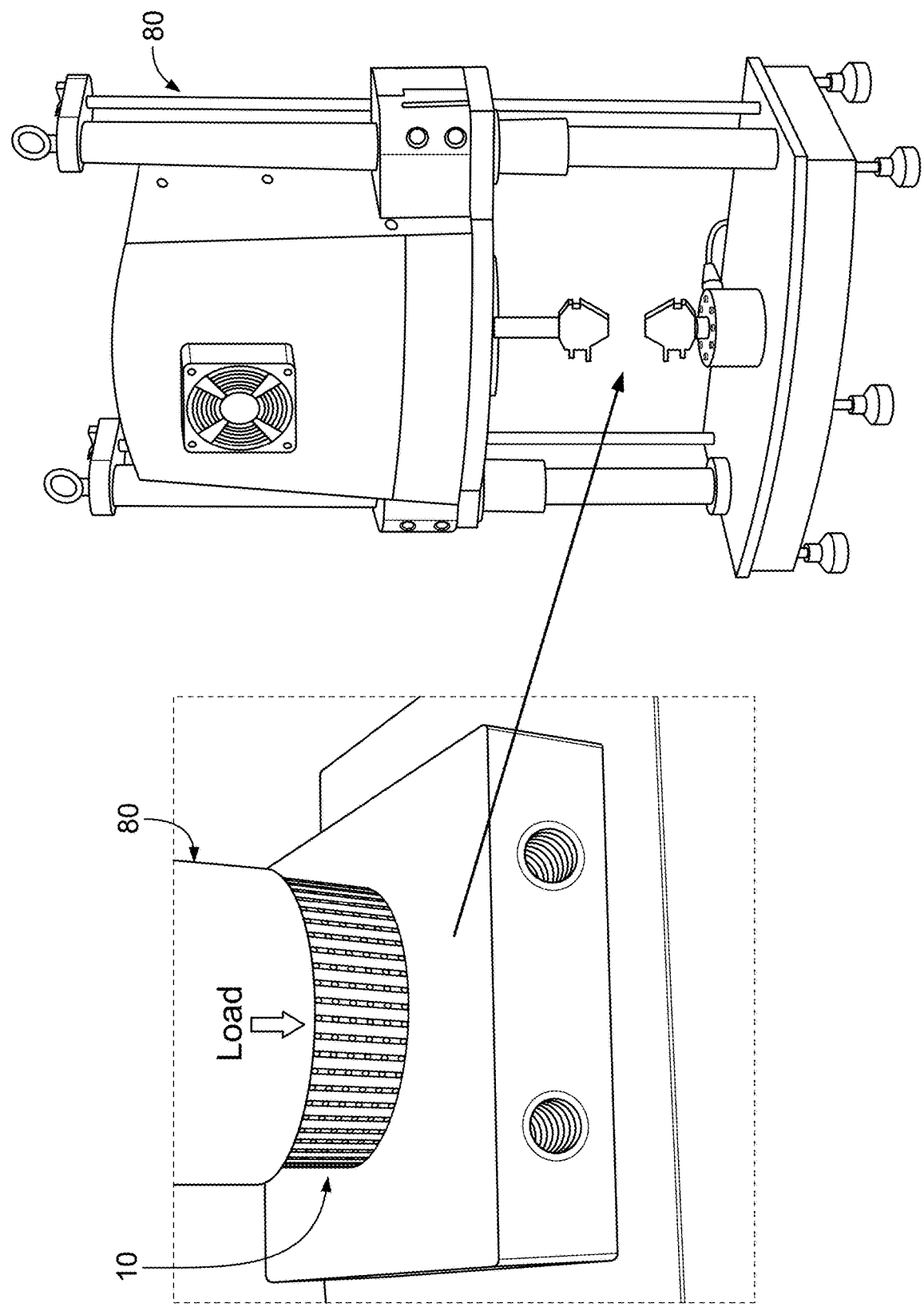
FIG. 41 is a schematic view of the experimental setup for mechanical testing of scaffolds according to an embodiment of the present invention after 28-day cell culture, as discussed in Example 1H herein.

The post-mechanically stimulated scaffolds 10 ((N=6) for each loading frequency group) were subjected to fatigue analysis by applying sinusoidal compressive loading at twice the adult torso weight from −75N to −750N for 1005 cycles at a rate of 2 Hz using a Bose ELF 3300 materials testing machine 80, as shown in FIG. 41. Native scaffolds, which contained no cells and were not subjected to any mechanical stimulation, were also mechanically tested using the parameters previously described (N=6). The deformation data was subjected to nonlinear analysis as previously described and subjected to a 1-way ANOVA, followed by Tukey post hoc test to compare differences in nonlinear regression parameters between the groups.

As shown in FIGS. 42A-D, all of the nonlinear regressions of the experimental groups (native, control, 0.5 Hz, 2 Hz, and 5 Hz) produced a two-phase decay fitting of the deformation data. Results of the parameters produced from a 1-way ANOVA were compared using Tukey's post hoc tests.

Figure 42A:
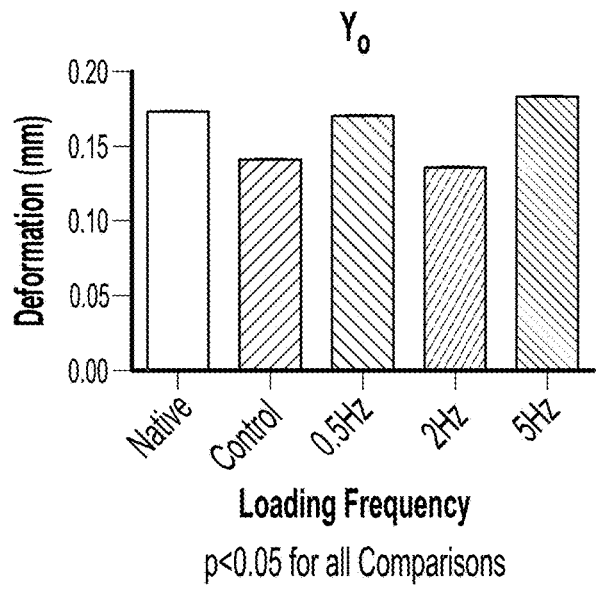
FIGS. 42A-D show the results of 1-ANOVA repeated measures testing with Tukey post hoc testing to statistically compare differences in loading frequency groups post 28-day mechanical stimulation, as discussed in Example 1H herein.
Figure 42B:
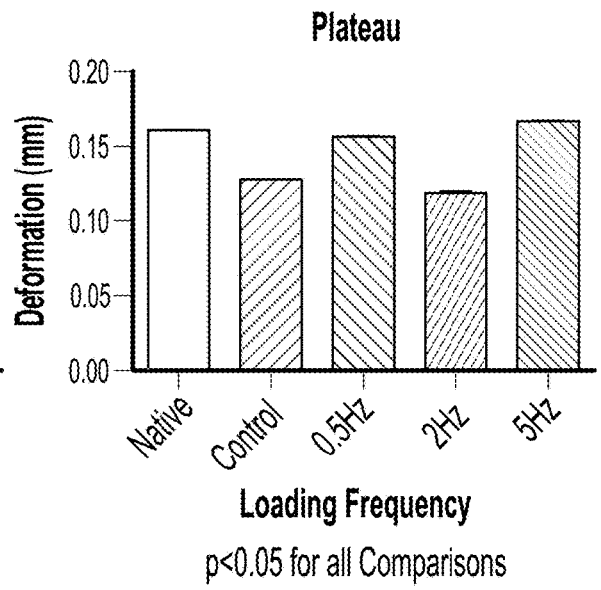

Regarding $Y_0$, the initial deformation, the comparison of all groups versus native scaffolds yielded statistical significance (p<0.05), as shown in FIG. 42A. A similar trend was observed with respect to Plateau values, as shown in FIG. 42B. With respect to Half-LifeFast values, with the exception of the control group all other groups were statistically significant (p<0.05). The 2 Hz loading frequency group possessed much higher Half-Life values compared to the rest of the groups, which may be correlated to its highly mineralized response over the course of the 28-day dynamic culture. A higher half-life can be indicative of long term load sustainment through pressurization of fluid within the scaffold (see FIG. 42C). It also had the highest Percent $K_{fast}$ compared to all other groups (see FIG. 42D), which may be indicative that it mineralized the greatest which resulted in increased stiffness at the end of the experiment, and therefore required less cycles to achieve stability.

Discussion

The need for scaffolds that facilitate both mechanical function and tissue regeneration still remains a key challenge in the field of regenerative medicine. There are still no well-approved treatment modalities that satisfy biological and mechanical requirements to achieve successful and secured healing. Despite recent advancements in achieving improved pore interconnectivity such as with computer controlled manufacturing methods, the need for scaffolds to also provide adequate mechanical function has not been met and is a fundamental requirement especially for defects in areas such as the femur or tibia, which are typically subjected to substantial weight bearing loads. To date, much of the focus in bone scaffold development regarding mechanical function has been on matching mechanical properties to mimic their respective anatomical sites and not enough on mechanical strength, which is problematic because while such scaffolds may demonstrate potential in vitro, they may fail under in vivo conditions due to inability to permit long term integration.

Thus, the objective of the foregoing examples entailed two major goals which addressed the mechanical and biological aspects of a scaffold designed for segmental bone replacement. The results of the mechanical and biological analyses demonstrate the potential for the scaffold of the present invention to revolutionize current standard treatments for segmental bone repair.

Scaffolds must maintain sufficient strength from the moment of implantation into the patient until the bone remodeling and fusion processes are complete. The rate of healing varies depending on the patient's case and with age, but for adults the point of weight bearing is approximately ten weeks post-trauma, while full mechanical integrity is reached approximately one year post-trauma. As the results of the fatigue endurance analysis reveal, at twice the torso weight of 800N, the scaffold was able to achieve stability at approximately 200,000 cycles, which correlates to ten weeks post-surgery (see FIG. 28). This is indicative that polymeric biodegradable scaffolds such as the scaffold of the present invention not only provide the structural and mechanical integrity required for fusion of bone defects, but also the potential to minimize use of metal fixation systems for structural reinforcement, thereby reducing the risk of bone resorption caused by stress shielding.

Based on results of the biological experiments, the scaffold of the present invention possesses the ability to sustain vascularity as bone proliferation and mineralization was observed throughout the 28-day mechanically stimulated dynamic culture. In these biological experiments human mesenchymal stem cells derived osteoblasts successfully mineralized, as confirmed the calcium deposits revealed by the Alizarin Red staining (see FIGS. 33A-36B). In translation to clinical use, an ideal scenario involves obtaining a biopsy of patient bone marrow cells to be dynamically cultured in vitro on the scaffold with mechanical stimulation, followed by implanting the tissue-engineered bone graft construct (i.e., the cell-seeded scaffold) back into the patient to initiate the healing process.

In the 28-day dynamic culture of the cell-seeded scaffolds, the alkaline phosphatase (ALP) activity and calcium content were quantitatively monitored, with Alizarin Red staining performed at the conclusion of the experiment. It was evident that there was more alkaline phosphatase activity and calcium deposition in the mechanically stimulated scaffolds, particularly the 2 Hz group, compared to the control group that was not subjected to daily loading. (p<0.05) (see FIGS. 37 and 39).

Alkaline phosphatase is an enzyme that occurs in nearly all living organisms. It has been well established that alkaline phosphatase plays an important role in the formation of hard tissue as it is highly expressed in mineralized tissue. ALP activity is correlated to its expression, and is regarded as a suitable marker for differentiation processes for various cell types such as stem cells within the bone marrow stromal cell population. Literature has reported that ALP enzyme activity is increased in early stages of osteoblast commitment and the upregulation of ALP during osteogenic differentiation reflects the quantity of osteogenic committed progenitor cells in a population. Therefore ALP activity, commonly utilized as a marker for osteogenic activity, was used to quantitatively assess the development of osteoblastic phenotype of the cells. This was achieved based on the use of a colorimetric assay which detects the conversion of p-nitrophenol phosphate to p-nitrophenol in the presence of alkaline phosphatase.

For all scaffold groups, the ALP activity decreased from the first to the second week (FIGS. 38A-D). It has been reported that a decrease in days 4-7 is not uncommon, as ALP activity declines as the developing osteoblasts become embedded into matrix as osteocytes. It has been hypothesized that once a matrix is established which encapsulates the cells, an elevated ALP level is not needed. ALP assists in the nucleation of mineral formation, and it is possible that this process forms quickly in scaffolds in the first seven days of seeding, thereby resulting in a reduction of ALP synthesis by the cells as it is not needed as much for mineralization of the surrounding matrix. Hoang et al. reported that ALP levels declines when other genes, such as osteocalcin, which promotes osteoblast adhesion, are upregulated.

All scaffold groups presented overall increase ALP activity as well as mineralization at the end of the 28-day dynamic culture, indicating a correlation between ALP activity and bone formation (see FIGS. 38A-D and 40A-D). Other studies demonstrated similar relationships. Further, Prins et al. demonstrated the in vivo bone forming capacity of bone marrow stromal stem cells may be predicted based on ALP levels during the in vitro osteogenic differentiation process. Therefore, results of this biological study show the potential to yield improved clinical outcome with respect to fusion procedures.

In in vitro studies involving osteogenic cultures, mineralization is considered as an endpoint as it reflects advanced cell differentiation. Calcium deposits are indicative of successful in vitro bone formation and can be specifically stained for visual purposes using Alizarin Red staining, a common method for quantifying calcification. Human bone marrow stem cells exhibit a two stage development process which entails slow proliferation during the first two weeks, expressing low ALP activity to produce and assemble a collagenous matrix. By the third week, matrix mineralized may be observed. Thus, it was critical to examine biological viability of the scaffolds for a minimum of 28-days. Regarding calcium content, all scaffold groups displayed a statistically increased trend from Day 1 to Day 28, with a greater incremental increase in the first three weeks (see FIG. 40A-D). Once the mineralization process is initiated, matrix synthesis increases rapidly in just a matter of days to 75% of the final mineral content. Maximum mineralization may take up to 1 year to achieve in order to radiographically visualize full fusion.

Figure 42C:
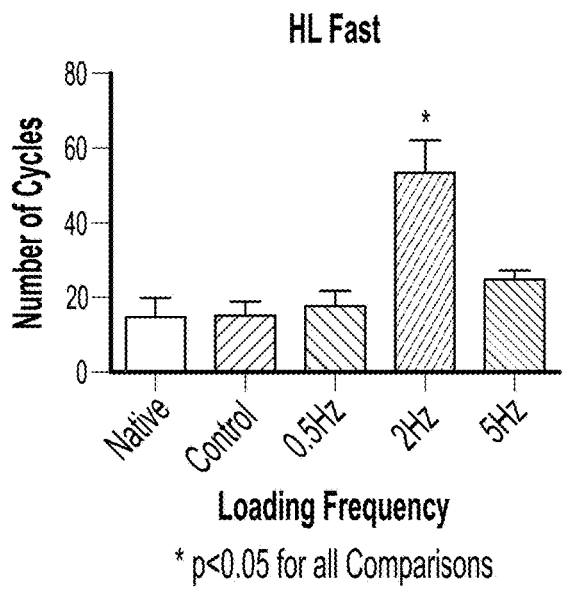
Figure 42D:
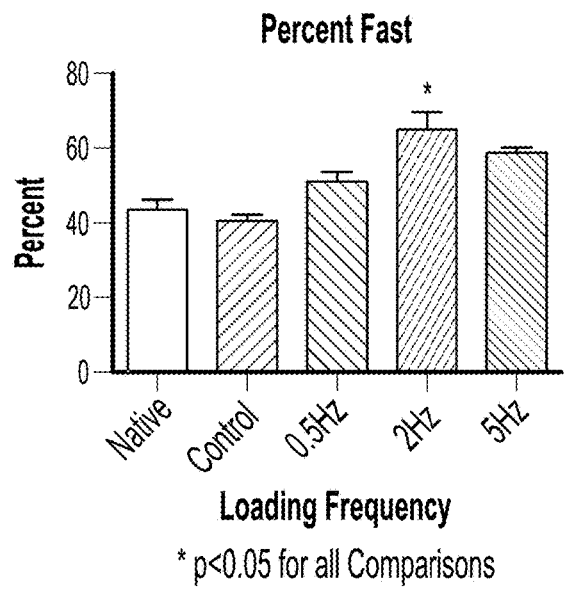

The statistical analysis of the post-mechanical stimulation fatigue testing data revealed that the 2 Hz loading frequency group possessed relatively higher half-life fast values as compared to the other groups, which may be correlated to its highly bone proliferative and mineralization response over the course of the 28-day dynamic culture (see FIG. 42C). Further, its higher Percent $K_{fast}$ as compared to the other groups is indicative of a relatively greater degree of mineralization, which perhaps reflects an increased stiffness thereby requiring less cycles to achieve and maintain stability. (see FIG. 42D) Studies have correlated the effects of scaffold stiffness on the osteogenic differentiation of mesenchymal stem cells, noting that cells respond greater to more rigid scaffolds by increasing their deposition of mineral content.

The response characteristics of this cell-seeded scaffold construct under daily mechanical stimulation is one of the few in vitro studies to examine frequency dependence on bone formation, as majority of studies have been focused on in vivo conditions. Based on the results of the biological experiments, it was evident that there was more alkaline phosphatase activity and calcium deposition in the mechanically stimulated scaffolds, particularly the 2 Hz group, compared to the control group that was not subjected to daily loading (see FIGS. 37A-E, 39A-D, and 42A-D) This is indicative that mechanical stimulation plays a role in facilitating the healing process of bone defects, so clinicians may want to consider that perhaps patients who undergo bone graft procedures should spend less time bed ridden to accelerate bone fusion as it has been cited that people walk with an average frequency of 2 Hz. Additionally, Duyuck et al. demonstrated the importance of mechanical loading in the early stages of healing around implants by evaluating the effects of implant displacement on tissue differentiation around loaded titanium implants. It was found that the degree of implant displacement had a significant effect on tissue differentiation around the immediately loaded implants. This emphasizes the need for mechanical stimulation for the differentiation and proliferation of new bone formation.

Cases of pediatric bone cancers are especially difficult to treat with respect to segmental bone repair as the patient's bone continues to grow after surgical implantation of a graft. Ozger et al. examined the resection and reconstruction methods in childhood bone and soft tissues of 68 patients with primary bone cancer in the lower extremity and noted that 20.6% of patients experienced shorted limbs. The ability of a bioresorbable and customizable scaffold that that can accommodate and align with patient's unique growth patterns would be ideal as it would ensure proper fitting and incorporation with the body. If patients required a revision surgery due to sudden abnormal growth, the cost and time to obtain a customized scaffold with respect to a sizable cadaveric graft is more cost efficient and significantly less traumatic.

The tibia possess a stiff outer shell of cortical bone that is thinnest in the epiphysis and thickest in the diaphysis, and within the epiphysis lies weaker trabecular bone as compared to the other regions of the long bone. This complex composition may influence its frequency response. Zhao examined a wide spectrum of loading frequencies in mice tibia to determine its dependence on enhancing bone formation in locations along the bone. It was found that the proximal sections responded strongly to low frequency loading where the midshaft and distal regions responded stronger to higher frequency loading. Thus, it would be essential to examine the dependence of bone formation on loading frequency along various regions along the long bone in future work. Additionally, identifying regional variations across different sites of bone to distinguish differences in bone types and areas of higher physiological loading are essential for the development of patient-specific scaffolds as bone grafts. In a recent study examining a cross section of the proximal femur, it was found that the anterior and medial regions possessed lower K-values which resulted in slower settling when subjected to dynamic load.

Figure 43:
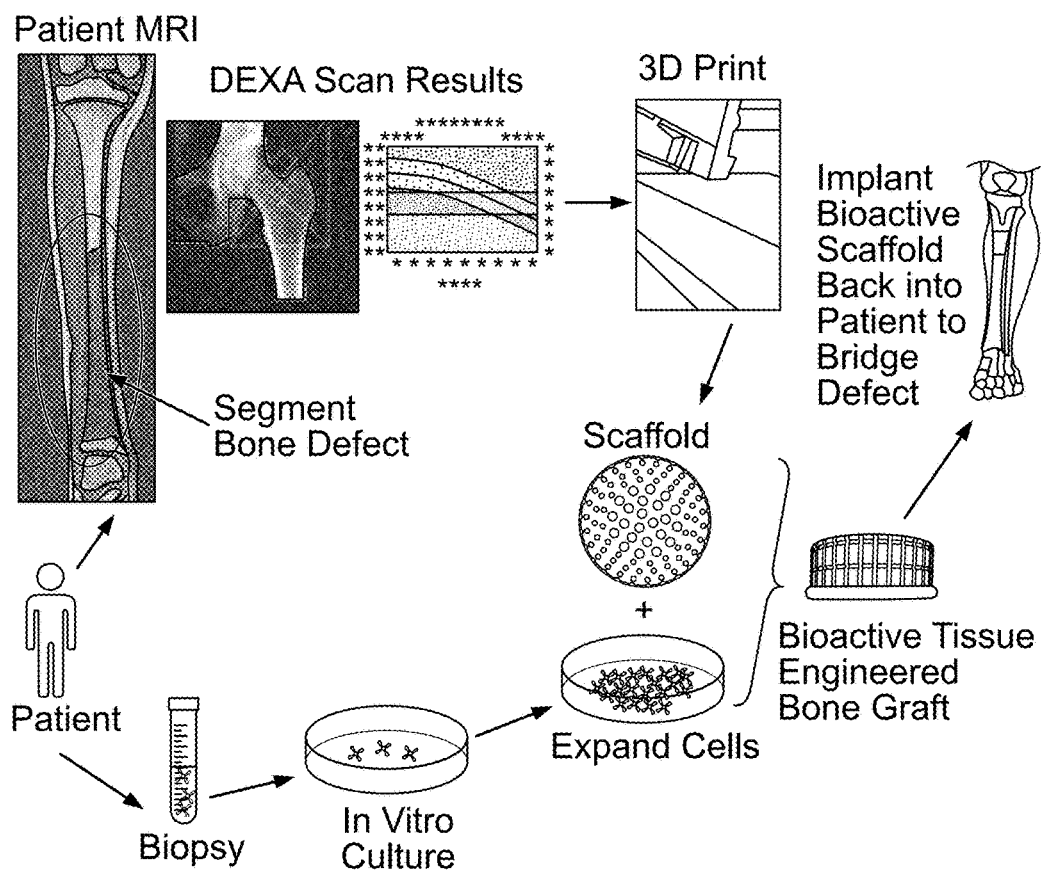
FIG. 43 is a schematic view of the process for achieving a patient-specific scaffold to be implanted into a patient for fusion of segmental bone defects.

Referring now to FIG. 43, bone densitometry (DEXA) scans are an established standard for measuring bone mineral density in patients, and may be useful in designing of patient-specific grafts as regions of varied bone volumes may be identified. Further, as the scaffold may be tailored to accommodate the bone defect geometry, it is also necessary to examine the cellular response of these patient-specific scaffolds to ensure stress shielding is not induced as stiffness would affect the strains acting on the cells that are attached to the scaffold. Bruels et al. noted that scaffold stiffness influences cell differentiation, growth, migration, and viability. Khatiwala et al. reported an increase in proliferation and mineral deposition of osteoblasts on harder substrates compared to softer substrates in a study culturing MC3T3-E1 cells on collagen-modified hydrogels with different stiffness.

CONCLUSION

A variable modulus scaffold was developed and fabricated by use of 3D printing. The presence of two appropriately located moduli improves the effectiveness in permitting integration at the implant-bone interface. The resulting increased modulus in the outer core of the scaffold provides a stable mechanical framework to minimize potential stress shielding, while also offering a platform for the onset of callus formation. Static and dynamic analyses of the 3D-printed polymeric scaffold confirm that it has similar mechanical properties to those of native bone, and an ability to withstand physiological loading to sustain long-term stability. Use of the scaffold may minimize the use of metal fixation systems typically used in the treatment of long bone defects, thereby reducing the propensity of stress shielding.

Assessment of the cellular response of cell-seeded scaffolds subjected to daily loading demonstrates that mechanical stimulation accelerates the differentiation, proliferation, and mineralization bone tissue, particularly at 2 Hz loading frequency, thereby validating the biological viability of the scaffold of the present invention. Further, use of 3D printing for fabrication enables a variety of scaffold designs and configurations as pore size, interconnected porosity, shape, and modulus may modified for different bone graft applications (e.g., a filler for bone cancer resections or trauma, or a fusion device in cases of surgery). Depending on the defect location along the long bone shaft, the relative porosity of the scaffold may be modified to account for changes in cortical bone thickness (see FIG. 15).

The design of the internal architecture of the scaffold and fabrication by use of 3D printing technology enables sustained mechanical strength and facilitation of bone ingrowth, thereby demonstrating significant potential to serve as the next generation implant for segmental bone replacement. The scaffold of the present invention possesses advantages as compared to current "gold standard" of autograft and allograft use. Fabrication of the scaffold of the present invention using traditional medical-grade titanium may be the first step in widespread acceptance utilizing additive manufacturing for implant fabrication, thereby shaping the future of orthopedic practice.

All examples and conditional language recited herein are intended for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It will be understood that the embodiments described herein are merely exemplary and that a person skilled in the art may make many variations and modifications without departing from the spirit and scope of the invention. All such variations and modifications are intended to be included within the scope of the invention and the appended claims.

We claim:

1. A long bone repair scaffold adapted for use in the repair of a defect located along the length of a long bone, said scaffold comprising:
    a body including a longitudinal axis alignable in a direction parallel to the length of a long bone to be repaired, an inner core having an outer circumference encircling said longitudinal axis of said body, and an outer core having an inner circumference encircling said longitudinal axis of said body and circumferentially engaging said outer circumference of said inner core, said inner core having a first porosity and a first modulus, and said outer core having a second porosity and a second modulus, wherein said second porosity is lower than said first porosity, and wherein said second modulus is greater than said first modulus;
    a first set of inner conduits extending within said inner core parallel to said longitudinal axis of said body;
    a second set of inner conduits extending within said inner core perpendicular to said longitudinal axis of said body;
    a first set of outer conduits extending within said outer core parallel to said longitudinal axis of said body, said conduits of said first set of outer conduits being dimensionally smaller than said conduits of said first set of inner conduits; and
    a second set of outer conduits extending within said outer core perpendicular to said longitudinal axis of said body, said conduits of said second set of outer conduits being dimensionally smaller than said conduits of said second set of inner conduits.

2. The long bone repair scaffold of claim 1, wherein said first set of inner conduits, said second set of inner conduits, said first set of outer conduits, and said second set of outer conduits collectively form an interconnected network of conduits.

3. The long bone repair scaffold of claim 2, wherein said network of conduits provide said body of said scaffold with an internal architecture that is configured to mimic the plywood anatomy of human bone.

4. The scaffold of claim 1, wherein said body further includes a superior surface having a plurality of pores, each pore of said plurality of pores having a transverse dimension.

5. The long bone repair scaffold of claim 4, wherein said transverse dimension is about 300 µm.

6. The long bone repair scaffold of claim 4, wherein at least some of said conduits of said first set of inner conduits are connected to at least some of said pores of said plurality of pores.

7. The long bone repair scaffold of claim 6, wherein at least some of said conduits of said first set of outer conduits are connected to at least some of said pores of said plurality of pores.

8. The long bone repair scaffold of claim 4, wherein said body further includes a solid base plate on a surface of said body opposite said superior surface, said conduits of said first set of inner conduits and said conduits of said first set of outer conduits terminating in said body proximate said base plate.

9. The long bone repair scaffold of claim 8, wherein at least some of said conduits of said first and second sets of inner conduits and at least some of said conduits of said first and second sets of outer conduits are adapted to receive bone grafting material.

10. The long bone repair scaffold of claim 2, wherein said network of conduits form a maze-like structure within said body of said scaffold.

11. The long bone repair scaffold of claim 1, wherein said first set of inner conduits, said second set of inner conduits, said first set of outer conduits and said second set of outer conduits have one or more cross-sectional shapes selected from the group consisting of spherical, circular and hexagonal cross-sectional shapes.

12. The long bone repair scaffold of claim 1, wherein said body has a height of about 9.5 mm and a diameter of about 32 mm.

13. The long bone repair scaffold of claim 1, wherein said conduits of said first set of inner conduits have a diameter of about 2 mm and a height of about 2 mm; said conduits of said second set of inner conduits have a diameter of approximately 0.825 mm and a length of about 2 mm; said conduits of said first set of outer conduits have a diameter of about 1.5 mm and a height of about 2 mm; and said conduits of said second set of outer conduits have a diameter of about 0.625 mm and a length of about 1.5 mm.

14. The long bone repair scaffold of claim 1, wherein said first modulus is similar to that of cancellous bone, and wherein said second modulus is similar to that of cortical bone.

15. The long bone repair scaffold of claim 1, wherein said body further includes a transition region between said inner core and said outer core.

16. The long bone repair scaffold of claim 15, wherein said inner core, said outer core and said transition region are configured to emulate the internal architecture and porosity pattern of human bone.

17. The long bone repair scaffold of claim 1, wherein said scaffold is configured to have a compressive failure rate that is 9600N and a compressive stiffness that is 16650 N/mm.

18. The long bone repair scaffold of claim 1, wherein said body of said scaffold is fabricated from polylactic acid (PLA).

19. The long bone repair scaffold of claim 18, wherein said body of said scaffold is fabricated via 3D printing.

20. The long bone repair scaffold of claim 1, wherein said body of said scaffold is fabricated from a biocompatible material selected from the group consisting of polymers, metals, ceramics, and combinations thereof.

\* \* \* \* \*